(12) United States Patent
Zeng et al.

(10) Patent No.: US 9,821,009 B2
(45) Date of Patent: Nov. 21, 2017

(54) METHOD FOR MODULATING MICRORNA CONTENT IN LIVING BEINGS AND THE USE THEREOF

(75) Inventors: Ke Zeng, Taizhou (CN); Chenyu Zhang, Taizhou (CN); Junfeng Zhang, Taizhou (CN); Haijin Li, Taizhou (CN)

(73) Assignee: JIANGSU MINGMA BIOTECH CO., LTD., Taizhou (CN)

( * ) Notice: Subject to any disclaimer, the term of this patent is extended or adjusted under 35 U.S.C. 154(b) by 552 days.

(21) Appl. No.: 13/641,074

(22) PCT Filed: Apr. 13, 2010

(86) PCT No.: PCT/CN2010/000489
§ 371 (c)(1),
(2), (4) Date: Nov. 13, 2012

(87) PCT Pub. No.: WO2011/127625
PCT Pub. Date: Oct. 20, 2011

(65) Prior Publication Data
US 2013/0078225 A1    Mar. 28, 2013

(51) Int. Cl.
| C12N 15/11 | (2006.01) |
| A61K 35/14 | (2015.01) |
| A61K 35/28 | (2015.01) |
| A61K 35/36 | (2015.01) |
| C12N 15/88 | (2006.01) |

(52) U.S. Cl.
CPC .............. *A61K 35/14* (2013.01); *A61K 35/28* (2013.01); *A61K 35/36* (2013.01); *C12N 15/111* (2013.01); *C12N 15/88* (2013.01); *C12N 2310/141* (2013.01); *C12N 2320/32* (2013.01)

(58) Field of Classification Search
CPC ................................ A61K 35/14; C12N 15/11
See application file for complete search history.

(56) References Cited

U.S. PATENT DOCUMENTS

2009/0202493 A1* 8/2009 Lu .................... C12N 15/113
424/93.2

FOREIGN PATENT DOCUMENTS

| CN | 101386848 | 3/2009 |
| WO | 2009036236 A1 | 3/2009 |
| WO | 2009147519 A1 | 12/2009 |

OTHER PUBLICATIONS

Luis et al. Circulation; 2004, 110:1868-1873.*
Kooijmans et al. (International Journal of Nanomedicine, 2012; 7:1525-1541).*
International Search Report for PCT Application, dated Apr. 13, 2010.
Jia, Yin, et al, "Application of microRNAs in diagnosis and treatment of tumor and other diseases," J Mol Diagn Ther, Mar. 2010, vol. 2, No. 2, pp. 123-127.
Pegtel, DM, et al, "Functional delivery of viral miRNAs via exosomes," PNAS, Apr. 6, 2010, vol. 107, No. 14, pp. 6328-6333.
Yuan, Alex, et al, "Transfer of microRNAs by embryonic stem cell microvesicles," PLoS One, Mar. 2009, 4(3): e4722.
Chen, et al. "Characterization of microRNAs in serum: a novel class of biomarkers for diagnosis of cancer and other diseases" Cell Research (published online Sep. 2, 2008) 18:997-1006.

* cited by examiner

*Primary Examiner* — J. E. Angell
(74) *Attorney, Agent, or Firm* — Edwin S. Flores; Daniel J. Chalker; Chalker Flores, LLP

(57) ABSTRACT

The present invention relates to a method for modulating miRNA content in living beings and the use thereof, whereof the miRNAs are delivered initiatively and selectively by microparticles/MVs/exosomes to the circulatory system and target cells/tissues to perform various functions. The invention provides a novel combination of molecules that mediates the inter-cellular communication: the miRNAs secreted by cells through cellular MVs. Meanwhile, the present invention also provides a method for preparing cellular MVs entrapping certain miRNAs, and, according to the regulation and modification of gene expression in cells and tissues with the miRNA-entrapping cellular MVs, provides a novel method for modulating miRNA content in living beings, which is effective and adoptable to all cell types.

6 Claims, 15 Drawing Sheets

METHOD FOR MODULATING MICRORNA CONTENT IN LIVING BEINGS AND THE USE THEREOF

CROSS-REFERENCE TO RELATED APPLICATION

This application is a U.S. National Phase Application of International Application No. PCT/CN2010/000489, filed Apr. 13, 2010.

FIELD OF INVENTION

The present invention relates to a method for modulating microRNA (miRNA) content in living beings and the use thereof; more particularly, a method for the targeted and effective regulation of miRNA content in living beings by introducing microvesicles (MVs) that carry miRNAs, the content of which has been modulated, so as to affect the physiological and pathological statuses of the target living beings, and the use of the said method in treatment and/or prevention of diseases.

BACKGROUND ART

Cellular microvesicles (MVs) are a category of bi-layer lipid membrane biologic vesicles, ranging between 10-500 nm in diameter. They were first reported as early as in year 1967 and named "platelet dust" since they were derived from platelets, containing vesicles and promoting agglutination. In vitro studies have found that each of endothelial cells, vascular smooth muscle cells, platelets, leucocytes, lymphocytes, erythrocytes, and the like are all able to secret MVs. According to their source, MVs can be divided into two categories: exosomes and shedding vesicles. Exosomes are secreted in the manner of exocytosis with multi-vesicular bodies (MVBs) when cells are stimulated, and shedding vesicles are secreted by direct budding. Presently, different names are given to shedding vesicles secreted by different cells, for example, those from neutrophil granulocytes and monocytes are called ectosomes, and those from platelets are called microparticles.

Two cellular MV generation pathways are already known: cellular activation and apoptosis, but till now it is uncertain that whether the cellular MVs generated in these two pathways are similar in size, composition, and physiological functions or not. The membrane components of cellular MVs, mainly consisting of lipids and proteins, depend on source cells, while the internal components of the cellular MVs are yet unknown. It is predicted that the cellular MVs play a part in intercellular communication, receptor delivery, signal triggering or cellular contact, probably as well as in stress reaction, inflammation reaction and tissue regeneration of organ defense systems. However, the definite physiological functions of cellular MVs have not been investigated clearly up yet to now.

Micro-ribonucleic acids (microRNAs, miRNAs) have been a hot spot recently. They are a class of single stranded ribonucleic acid molecules that consist of about 19-23 nucleotides in length, locate in non-coding regions in the genome and are highly conserved in evolution. MiRNAs may regulate gene expression by inhibiting the translation of their target genes, and are closely related to many physiological actions of animals, such as individual development, tissue differentiation, cell apoptosis and energy metabolism, and etc., as well as to the occurrence and progression of various diseases. Since the discovery of lin-4 and let-7 involved in the regulation of timing development of nematodes, miRNAs have become a hot spot in the field of regulation of miRNA stability and protein translation and are selected as one of top 10 scientific breakthroughs of Science in year 2002 and 2003 successively. Now, it is predicted that the miRNAs can at least regulate 5,300 human genes, that is, 30% of all human genes. More and more miRNAs have been found in further research, wherein the relations between miRNAs and tumors are becoming an important point in primary study. It has been found that several miRNAs are closely related to chronic lymphocytic leukemia, lung cancer, breast cancer, and colon carcinoma by negative regulation of gene expression. Recently, it has been found that the expression levels of several miRNAs in both chronic lymphocytic leukemia and Burkitt's lymphoma are down-regulated to certain extents. Analysis on the expression of the miRNAs in human lung cancer and breast cancer tissues shows that the expression levels of several tissue-specific miRNAs vary relative to normal tissues. Other studies have also demonstrated that the miRNAs affect the occurrence and progression of cardiovascular diseases, including myocardial hypertrophy, heart failure, atherosclerosis and etc., and are closely related to metabolic diseases such as diabetes type II. These experimental results indicate that the expression of the miRNAs and the specificity variations thereof are inevitably related to the occurrence and progression of the diseases.

MiRNAs play a highly important role in gene post-transcriptional regulation, which indicates that the relation between miRNAs and diseases is: firstly, the variations of miRNAs may be the result of diseases, because the occurrence of diseases (cancers, for instance) will cause chromosome segments loss, gene mutation or sudden amplification of chromosome segments. If the miRNAs are located in such varied segments, their expression levels will vary tremendously. Secondly, the variations of miRNAs may be the cause of diseases, because the disease inhibition and promotion factors are probably the targets of miRNAs. When there are miRNA expression disorders, for example, when expression level of miRNAs that inhibit the disease promotion factors is down-regulated, or the expression level of the miRNAs that inhibit the disease inhibition factors is up-regulated, the down-stream gene expression will be altered and there comes pathway disorder, eventually causing the occurrence of the diseases. On the contrary, if the expression level of miRNAs that inhibit the disease promotion factors is up-regulated, or the expression level of miRNAs that inhibit the disease inhibitory factors is down-regulated, the down-regulation of a series of disease promotion factors will be caused, and thereby the occurrence or progression of diseases will be inhibited. Therefore, theoretically, miRNAs can be used not only as a novel class of disease markers—their specificity variations are necessarily related to the occurrence and progression of the diseases; but also potential drugs, the occurrence and progression of the diseases may be largely relieved by inhibiting the miRNAs whose expression levels are up or down-regulated during the disease progression. Therefore, it is rather significant for the prevention and/or treatment of various diseases to develop a drug that can regulate the miRNA content in patients, so as to up-regulate the disease inhibitory factors, or down-regulate the disease promotion factors.

In recent years, miRNA medicine has been a hot spot of pharmaceutical development. It has been proved that the progression of diseases could be inhibited or deferred by regulating the expression of certain miRNAs. For instance, highly expressed miR-206 in skeletal muscles could relieve the motor neuron injury or loss, which is achieved by improving and activating the regeneration of neuron connections between muscles, whereby can treat Amyotrophic lateral sclerosis (ALS). Similarly, HCV can be treated by down-regulating miR-122 expression in liver. Loss of miR-15 and miR-16 results in over-expression of Bal-2, which is the key cause of chronic lymphatic leukemia (CLL), and thus up-regulating the expression of miR-15 and miR-16 shall be an effective way to cure CLL.

Although the research and exploration on miRNA medicine has got many achievements, some problems still hinder their practical use, with the biggest one being the insufficient efficiency and inadequate ability of targeted drug delivery. Presently, the miRNA carriers mainly include liposome, nanocapsules (or nanoparticles), β-cyclodextrin inclusion compound, and etc. Although they can prolong the drug retention in vivo and promote drug absorption to some extent, their targeted ability and efficiency in drug delivery are still unsatisfactory. Virus vectors can also promote drug delivery in vivo, but their potential threat to living beings restrains their application in miRNA drug delivery. Further research shall be done on the effective drug administration on human beings or animals, insuring both effective and secure drug delivery to the target organs/tissues.

DISCLOSURE OF THE INVENTION

To sum up, to apply miRNAs as potential pharmaceutical treatment, some problems are still unsolved. Besides that the target genes of miRNAs are still unclear, the delivery of miRNAs bears shortages including poor targeted ability, low efficiency and insufficient security.

In studies on the application of miRNAs as disease markers, the inventor has found that miRNAs exist stably in human serum/plasma and cell-culture medium, and that these miRNAs are closely related to pathological and physiological statuses of human body, including malignant oncogenesis, immunologic deficiency, inflammation generation, and the like. Basing on systemic studies on serum/plasma miRNAs, the inventor initiates the proposal of using serum/plasma miRNAs as novel diagnosis indicators. Further investigation on the source of miRNAs in serum/plasma and cell-culture medium discovers that most of miRNAs in serum/plasma and cell culture medium are delivered by cellular MVs. Cellular MVs are variable in size, ranging between 10-500 nm. It shall be noted that the cellular MVs in serum are not only secreted by blood cells, but also by cells in other human tissues, such as vascular endothelial cells, cells in lung and liver tissues, and etc. In pathogenic statuses, tumor cells and pathogens can secrete or induce cells to secrete MVs. These MVs entrap specific miRNAs, and bind specifically to immune cells to deliver the miRNAs into them, thus silencing their functions and eventually protecting the tumors and pathogens from being attacked. The present application has confirmed in researches that the membrane components (including surface specificity receptors and lipid membrane structure) of MVs secreted by different cells are the same as the plasma membrane components of the source cells, and that the types of the MV-entrapped miRNA are relative to miRNAs in the source cells. Therefore, cellular MVs possess the same receptor proteins or lipid membrane structure unique to the surface of the source cells, have high affinity to the corresponding target cells and can selectively deliver miRNAs into the target cells/tissues, thus remarkably enhancing the regulation of cellular functions by the miRNAs. Since the cellular MVs (including the lipid vesicular structures with functions similar to the cellular MVs, such as exosomes, shedding vesicles and certain shedding vesicles secreted by different cells) possess the capacity of specifically binding to particular tissues and cells, the cellular MV-entrapped miRNAs also exhibit high targeted ability, stability and efficiency, showing significant prospect for their applications in pathogenesis study and disease treatment.

Therefore, the present invention is aimed to provide a method for modulating miRNA content in living beings by delivering miRNAs into living beings specifically and efficiently.

To achieve the aforesaid purpose, the technical solutions applied are as follows:

A method for modulating miRNA content in living beings, including the following steps:
  (1) modulating miRNA content entrapped in the cellular MVs of donor cells;
  (2) separating the donor cellular MVs; and
  (3) delivering the separated MVs into the target living beings.

In the method according to the present invention, the source of the cellular MVs of the donor cells can be selected from the group consisting of one or more of body fluids, preferably blood; cell culture media and tissues.

In the method according to the present invention, the step that modulating miRNA content entrapped in the cellular MVs of donor cells is either up or down-regulating the miRNA level in the MVs of the donor cells, in which the up-regulation of the donor cellular MV-entrapped miRNAs can be exerting exogenous stimuli and/or introducing miRNA precursors. Preferably, the exertion of exogenous stimuli includes the following steps: exerting one or more exogenous stimuli, such as hormones, cellular factors, lipopolysaccharides, free fatty acids, advanced glycosylation end products and $H_2O_2$, which can affect the cell inflammation reaction, metabolism, life cycles and functions, and then incubating. Preferably, the introduction of miRNA precursors includes the following steps: introducing certain miRNA precursors into the cells with liposome carriers (Invitrogen Co., Lipofectamine 2000), and then incubating. Therein, the method of down-regulating the content of donor cellular MV-entrapped miRNA is to exert exogenous stimuli and/or introduce the antisense RNAs of the miRNAs. Preferably, the exertion of exogenous stimuli includes the following steps: exerting on cells cultured in vitro one or more exogenous stimuli, such as hormones, cytokines, lipopolysaccharides, free fatty acids, advanced glycosylation end products and $H_2O_2$, which can affect the inflammation, metabolism, life cycle and functions of the cells, and then incubating. Preferably, the introduction of antisense RNAs of miRNAs includes the following steps: using liposome carrier (Invitrogen Co., Lipofectamine, 2000) to introduce the corresponding antisense RNAs of miRNAs into the cells, and then incubating.

In the method according to the present invention, separating donor cellular MVs can be one or more methods selected from the group consisting of fractional centrifugation, immune-adsorption and ultra-filtration.

Particularly, the fractional centrifugation can comprise the following steps:
  (1) performing centrifugation on the donor, for example, the cell culture medium, tissue or body fluid, at 300 g for 5 min, and recovering the first supernatant;
  (2) performing centrifugation on the first supernatant at 1,500 g for 20 minutes, and recover the second supernatant;

(3) performing centrifugation on the second supernatant at 10,000 g for 30 minutes, and recovering the third supernatant; and
(4) performing centrifugation on the third supernatant at 110,000 g for 70 minutes, and the pellet is the donor cellular MVs.

Particularly, the immune-adsorption can comprise the following steps:
(1) performing centrifugation on the donor, for example, the cell culture medium, tissue or body fluid, at 3,000 rpm for 30 minutes, and recovering the supernatant; and
(2) incubating the supernatant in the tissue culture plates absorbed with cell-specific antibodies or immunomagnetic beads for 30 to 60 minutes, and recovering the absorbed cellular MVs;

Particularly, the ultra-filtration can comprise the following steps:
(1) performing centrifugation on the donor, for example, the cell culture medium or tissue or body fluid, at 3,000 rpm for 30 minutes, and recovering the supernatant; and
(2) placing the supernatant into a concentrating centrifuge tube with filter membranes of 100 kD MWCO, performing centrifugation at 4,000 rpm, and then recovering cellular MVs after concentration.

In the method according to the present invention, the living being can be one or more selected from the group consisting of human beings; animals, such as cartilaginous fish, bony fish, amphibians, reptiles, birds and mammals; microorganisms, such as bacteria, leptospirae, mycoplasmata, Rickettsiae, Chlamydiae, actinomycetes and viruses. Particularly, the viruses can be one or more selected from the group consisting of DNA and RNA viruses, such as hepatitis B viruses, smallpox viruses, anthrax bacilli, HIV, SARS viruses and influenza viruses.

The present invention also provides a method for preventing and/or treating diseases, which includes using the above-mentioned method for regulating the content of miRNAs in living beings to modulate the content of disease-related miRNAs in human beings or animals, in which the up or down-regulation of the content of miRNA is related to the occurrence and progression of the diseases.

The above-mentioned diseases can be one or more selected from the group consisting of tumors; acute and chronic infectious disease, such as viral diseases including viral flu, viral hepatitis, AIDS, SARS and etc., and such as bacterial diseases including TB, bacterial pneumonia and etc., and such as other acute and/or chronic diseases caused by other pathogenic microorganisms; diseases of respiratory system; diseases of immune system; diseases of blood and hematopoietic system; diseases of circulatory system such as cardio-cerebrovascular diseases; diseases of endocrine system; diseases of digestive system; diseases of neural system; diseases of urinary system; diseases of reproductive diseases and diseases of locomotor system. Particularly, the above-mentioned diseases can be one or more selected from the group consisting of atherosclerosis, adiposity caused by blood vessel injury, hyperglycemia and chronic inflammation.

The miRNA relevant to the disease is one or more selected from the group consisting of miRNAs, such as let-7b, let-7c, let-7d, let-7, elet-7f, let-7g, let-71, miR-1, miR-100, miR-101, miR-103, miR-105, miR-106a, miR-106b, miR-107, miR-10a, miR-10b, miR-122a, miR-124a, miR-125a, miR-125b, miR-126, miR-126*, miR-127, miR-128a, miR-128b, miR-129, miR-130a, miR-130b, miR-132, miR-133a, miR-133b, miR-134, miR-135a, miR-135b, miR-136, miR-137, miR-138, miR-139, miR-140, miR-141, miR-142-3p, miR-142-5p, miR-143, miR-144, miR-145, miR-146a, miR-146b, miR-147, miR-148a, miR-148b, miR-149, miR-150, miR-151, miR-152, miR-153, miR-154, miR-154*, miR-155, miR-15a, miR-15b, miR-16, miR-17-3p, miR-17-5p, miR-181a, miR-181b, miR-181c, miR-181d, miR-182, miR-182*, miR-183, miR-184, miR-185, miR-186, miR-187, miR-188, miR-189, miR-18a, miR-18a*, miR-18b, miR-190, miR-191, miR-191*, miR-192, miR-193a, miR-193, miR-194, miR-195, miR-196a, miR-196b, miR-197, miR-198, miR-199a, miR-199a*, miR-199b, miR-19a, miR-19b, miR-200a, miR-200a*, miR-200b, miR-200c, miR-202, miR-202*, miR-203, miR-204, miR-205, miR-206, miR-208, miR-20a, miR-20b, miR-21, miR-210, miR-211, miR-212, miR-213, miR-214, miR-215, miR-216, miR-217, miR-218, miR-219, miR-22, miR-220, miR-221, miR-222, miR-223, miR-224, miR-23a, miR-23b, miR-24, miR-25, miR-26a, miR-26b, miR-27a, miR-27b, miR-28, miR-296, miR-299-3p, miR-299-5p, miR-29a, miR-29b, miR-29c, miR-301, miR-302a, miR-302a*, miR-302b, miR-302b*, miR-302c, miR-302c*, miR-302d, miR-30a-3p, miR-30a-5p, miR-30b, miR-30c, miR-30d, miR-30e-3p, miR-30e-5p, miR-31, miR-32, miR-320, miR-323, miR-324-3p, miR-324-5p, miR-325, miR-326, miR-328, miR-329, miR-33, miR-330, miR-331, miR-335, miR-337, miR-338, miR-339, miR-33b, miR-340, miR-342, miR-345, miR-346, miR-34a, miR-34b, miR-34c, miR-361, miR-362, miR-363, miR-363*, miR-365, miR-367, miR-368, miR-369-3p, miR-369-5p, miR-370, miR-371, miR-372, miR-373, miR-373*, miR-374, miR-375, miR-376a, miR-376a*, miR-376b, miR-377, miR-378, miR-379, miR-380-3p, miR-380-5p, miR-381, miR-382, miR-383, miR-384, miR-409-3p, miR-409-5p, miR-410, miR-411, miR-412, miR-421, miR-422a, miR-422b, miR-423, miR-424, miR-425, miR-425-5p, miR-429, miR-431, miR-432, miR-432*, miR-433, miR-448, miR-449, miR-450, miR-451, miR-452, miR-452*, miR-453, miR-455, miR-483, miR-484, miR-485-3p, miR-485-5p, miR-486, miR-487a, miR-487b, miR-488, miR-489, miR-490, miR-491, miR-492, miR-493, miR-493-3p, miR-494, miR-495, miR-496, miR-497, miR-498, miR-499, miR-500, miR-501, miR-502, miR-503, miR-504, miR-505, miR-506, miR-507, miR-508, miR-509, miR-510, miR-511, miR-512-3p, miR-512-5p, miR-513, miR-514, miR-515-3p, miR-515-5p, miR-516-3p, miR-516-5p, miR-517*, miR-517a, miR-517b, miR-517c, miR-518a, miR-518a-2*, miR-518b, miR-518c, miR-518c*, miR-518d, miR-518e, miR-518f, miR-518f*, miR-519a, miR-519b, miR-519c, miR-519d, miR-519e, miR-519e*, miR-520a, miR-520a*, miR-520b, miR-520c, miR-520d, miR-520d*, miR-520e, miR-520f, miR-520g, miR-520h, miR-521, miR-522, miR-523, miR-524, miR-524*, miR-525, miR-525*, miR-526a, miR-526b, miR-526b*, miR-526c, miR-527, miR-532, miR-542-3p, miR-542-5p, miR-544, miR-545, miR-548a, miR-548b, miR-548c, miR-548d, miR-549, miR-550, miR-551a, miR-552, miR-553, miR-554, miR-555, miR-556, miR-557, miR-558, miR-559, miR-560, miR-561, miR-562, miR-563, miR-564, miR-565, miR-566, miR-567, miR-568, miR-569, miR-570, miR-571, miR-572, miR-573, miR-574, miR-575, miR-576, miR-577, miR-578, miR-579, miR-580, miR-581, miR-582, miR-583, miR-584, miR-585, miR-586, miR-587, miR-588, miR-589, miR-590, miR-591, miR-592, miR-593, miR-594, miR-595, miR-596, miR-597, miR-598, miR-599, miR-600, miR-601, miR-602, miR-603, miR-604, miR-605, miR-606, miR-607, miR-608, miR-609, miR-610, miR-611, miR-612, miR-613, miR-614, miR-615, miR-616, miR-617, miR-618, miR-619, miR-620, miR-621, miR-622, miR-623, miR-624, miR-625, miR-626, miR-627, miR-628, miR-629, miR-630, miR-631, miR-632, miR-633, miR-634, miR-635, miR-636, miR-637, miR-638, miR-639, miR-640, miR-641, miR-642, miR-643, miR-644, miR-645, miR-646, miR-647, miR-648, miR-649, miR-650, miR-651, miR-652, miR-653, miR-654, miR-655, miR-656, miR-657, miR-658, miR-659, miR-660, miR-661, miR-662, miR-663, miR-7, miR-9, miR-9*, miR-92, miR-93, miR-95, miR-96, miR-98, miR-99a and miR-99b, like one or more than one of miR-16, miR-26a, miR-29a, miR-30c, miR-125b, miR-138, miR-142-3p, miR-150, miR-181a, miR-181b, miR-136, miR-146a, miR-222 and miR-451. One particular example can be one or more miRNAs selected from the group consisting of miR-125b, miR-16, miR-142-3p, miR-451 and miR-150. More particular examples are miR-451 and miR-150, or miR-150.

The above-mentioned method to prevent and/or treat diseases starts with modulating the content of donor cellular MV-entrapped miRNAs that can affect the occurrence and progression of diseases, then separates and prepares such treated cellular MVs, and introduces them into the recipient cells or injects them into the patient's body, so that the miRNA-entrapping cellular MVs can enter into the recipient cells or the diseased tissue; by the interaction between the miRNAs and their target genes, the expression of the target genes and the corresponding proteins is regulated, consequently the cell functions are affected, and thereby the prevention and/or treatment of diseases is achieved.

In order to detect in vitro the influence on the intercellular or inter-tissue physiological functions and the function pathways formed by the miRNA-entrapping cellular MVs, the invention applies the following techniques: confocal fluorescence microscopy, Real-time PCR technique, the cell transfection method, Western Blotting technique and the cell migration method.

The confocal fluorescence microscopy includes steps as follows: labeling the cells with diI-C16; rinsing the cells with PBS; re-suspending the cells in a RPMI 1640 medium containing 10% FBS at 37° C. overnight; removing the supernatant and collecting the cellular MVs by centrifugation; re-suspending the recovered cellular MVs in another cell type and incubating them under different time gradients; rinsing the cells, fixing them and observing under the confocal microscopy.

The cell migration method includes steps as follows: covering the polycarbonate membrane (8 μm in pore diameter) at the bottom of the upper chamber in the Transwell Boyden Chamber (6.5 mm, Costar, Cambridge, Mass., USA) with 0.1% of gelatin; suspending the cells in a serum-free culture medium, and limiting the concentration within $(1\text{-}10) \times 10^5$ cells/ml; incubating the cells with or without cellular MVs derived from another type of cells for 2 hours, and adding them into the upper chamber, and filling 0.5 ml of culture medium containing 10% fetal bovine serum into the lower chamber; incubating the cells in the culture incubator in a 5% of $CO_2$ atmosphere for 4 hours; fixing the cells that have migrated into the lower chamber with 90% of ethanol at the room temperature for 15 minutes; rinsing the fixed cells; staining the cells with 0.1% of crystal violet at the room temperature for 15 minutes; scraping carefully the cells retaining on the filter membrane down and taking photos of them (Olympus, BX51, Japan); counting the cells.

In order to detect in vivo the influence on the intercellular or inter-tissue physiological functions and functional pathways formed by the miRNA-entrapping cellular MVs, the invention applies the following procedure: intravenously injecting the cellular MVs into the mice tails and detecting the miRNA content entrapped in the cellular MVs in the mouse blood vessel walls, and then observing the influence on the mouse blood vessel endothelial cells from the cellular MVs labeled with fluorescence and injected intravenously into the mice tails.

In which, the intravenous injection of the cellular MVs into the mice tails and detection of miRNA content in the mouse blood vessel walls comprises the following steps:
(1) separating the cellular MVs from one type of cells;
(2) injecting intravenously the cellular MVs into the mice tails;
(3) extracting the RNA from the mouse blood vessel;
(4) detecting the variations of the miRNAs in vascular tissues of normal mice and in that of mice injected with the cellular MVs from another type of cells by the Real-time PCR technique.

In which, the detection under microscope of the influence on the blood vessel endothelial cells from the fluorescence labeled cellular MVs injected into the mouse caudal veins includes the following steps:
(1) conducting fluorescence labeling on cellular MVs;
(2) injecting the cellular MVs into the tail veins of mice;
(3) separating the endothelium of mouse blood vessels;
(4) observing under fluorescent microscope.

Presently, as traditional signaling molecules, hormones and cytokines can bind with acceptor molecules in target cells and regulate intercellular communication, but they act only on some specific kinds of cells, because only the specific cells can excrete hormones and cytokines. In other words, no intercellular communication pathway that can be adopted by all kinds of cells is found, and there is no reports concerning that miRNAs initially and selectively secreted by cellular MVs are as a novel family of signaling molecules that can be adopted by all kinds of cells. Basing on the discovery about cellular MV-entrapped miRNAs, the inventor focuses on the targeting ability, stability and efficiency of miRNA-entrapping cellular MVs (or lipid vesicular structures similar to cellular MVs), and their application prospect in the research of biological signaling mechanisms, discovery of new pathological mechanisms and disease treatment regimens. Since miRNAs are a novel type of disease biomarkers, basing on the studies in terms of the existence, detectability and relativity to the target cells and diseases of cellular MV-entrapped miRNAs in serum/plasma and tissue/cell culture medium, the inventor seeks to establish a novel technique that can be adopted in researches for new intercellular communication pathways, pathological mechanisms and disease treatment regimens, and etc. by making use of the cellular MV-entrapped miRNAs existing stably in serum/plasma and tissue/cell culture medium. Therefore, the purpose of the present invention is to provide a method and its application for regulating miRNAs in cellular MVs.

The inventor has performed experiments on the delivery of miRNAs with cellular MVs as vectors into the target cells. Cellular MVs are cell-derived and thus bio-compatible, exerting no damage to the living bodies. Besides, the cellular MVs carry molecules that are cell-derived and cell membrane specific, they can deliver the entrapped miRNA medicines effectively and specifically into the target cells/tissues by combining with receptor/ligand in the target cell membrane. The miRNAs delivered into the target cell/tissue can block the translation of target genes into proteins by combining with the target genes—specific sequences of mRNAs and thereby achieve the specific blockage of gene expression.

Based on the series of researches mentioned above, the present invention provides a type of miRNAs: the miRNAs entrapped by cellular MV (or lipid vesicular structures similar to cellular MVs), which possess stronger targeting ability and stability and higher efficiency and significant prospects in the application in researches on pathological mechanism and disease treatment. Besides, the invention also proves that the prevention and treatment of the diseases can be achieved by modulating the content of cellular MV-entrapped miRNAs.

The problems that shall be solved in the invention are: (1) to investigate the relativity between various clinical diseases (including various tumors; various acute and/or chronic infectious diseases, and other acute and/or chronic infectious diseases caused by pathogenic microbes; other acute and/or chronic diseases, such as respiratory system diseases, immune system diseases, blood and hematopoietic system diseases, for example, cardio-cerebrovascular diseases, circulation system diseases, endocrine and metabolic system diseases, digestive system diseases, nervous system diseases, urinary system diseases, reproductive system diseases and locomotor system diseases) and cellular MV-entrapped miRNAs; (2) to modulate cellular MV-entrapped miRNA content, prepare in vitro the cellular MVs entrapping particular miRNAs and then introduce the cellular MVs into the target body, so that the aforesaid miRNAs can be delivered to the specific cells/tissues based on the stability and targeting ability of the cellular MVs, thus improving the functions of tissues and treatment of diseases.

The use of cellular MV-entrapped miRNAs for treatment of diseases features the following advantages:
  (1) The cellular MVs have the properties of host cells, the kinds and variations of the cellular MVs and the cellular MV-entrapped miRNAs can directly identify cells of disease focus.
  (2) As a novel, stable and highly specific delivery tool, cellular MVs can efficiently introduce particular miRNAs into target cells/tissues, thus improving the cell status and treatment of diseases.

In conclusion, the cellular MVs and miRNAs entrapped within them do not only provide a material basis for comprehensive understanding of the intercellular signaling pathways and tissue pathogenesis at the molecular level, but also promote the progress of the clinical diagnosis and therapy. Of course, most of the molecular techniques applied in the early researches on the pathogenesis, diagnosis and treatment of diseases are still in the starting experimental stage and their effectiveness shall be further investigated and improved. However, due to the advantages of the cellular MVs and miRNAs entrapped therein, the study on the pathogenesis of severe diseases, such as cancer, and specific treatment for these diseases shall be achieved in the future with the application of the cellular MVs and miRNAs entrapped therein.

BRIEF DESCRIPTION OF THE DRAWINGS

The examples of the invention will be illustrated in combination with the accompanying drawings, wherein.

PREFERRED EMBODIMENTS OF THE INVENTION

It should be understood that the embodiments described specifically herein are the examples, which are not intended to limit the scope of the invention. The major features of the present invention can be applied in various embodiments without departing from the scope of the invention. It will be recognized and ensured by a person skilled in the art that the conventional experiments and many equivalents thereof all are able to be applied in certain steps described above. Such equivalents are believed to be within the scope of the invention and covered by the appended claims.

Example 1: Solexa Sequencing of Serum and Blood Cells/Tissues

It is found with Solexa sequencing technique that the miRNAs in serum is negatively correlated with those in blood cells/tissues.

Solexa sequencing of serum and blood cells comprises the following steps:
(1) collecting blood samples of normal subjects and non-small-cell lung cancer patients;
(2) separating serum from blood cells by centrifugation;
(3) extracting the total RNA, and extracting cell RNAs for Solexa sequencing by using Trizol reagent (Invitrogen Co.); particularly, the extraction of serum RNA for Solexa sequencing includes the following steps: adding acidic phenol into 100 µl of sample and shaking up; adding chloroform into the solution and shaking up again; centrifuging the mixed solution at 12000 g at the room temperature for 10 minutes; extracting carefully the first supernatant, adding 1000 µl of ethanol and 40 µl of sodium acetate into the first supernatant; blending the mixed solution sufficiently, placing it at the room temperature for 10 minutes, and then centrifuging it at 16000 g under 4° C. for 20 minutes; removing the second supernatant, and adding 75% 1 ml of ethanol into the sediment; blending the solution gently for several times, and centrifuging it at 16000 g under 4° C. for 10 minutes, removing the third supernatant, and drying the sediment at the room temperature; adding 20 µl of DEPC solution into the dried sediment; mixing all the samples treated in the same way, and adding isometric isopropyl alcohol with the same volume into the samples, blending the mixed solution evenly, and centrifuging at 16000 g under 4° C. for 20 minutes; removing the fourth supernatant completely, and drying the sediment at the room temperature; dissolving the dried sediment into 100 µl of DEPC solution; the proper amount of samples is extracted for RNA detection with ultraviolet spectrophotometer; and
(4) conducting Solexa sequencing with reference to the particular steps in the operation instructions by Illumine Co.

Figure 1A:
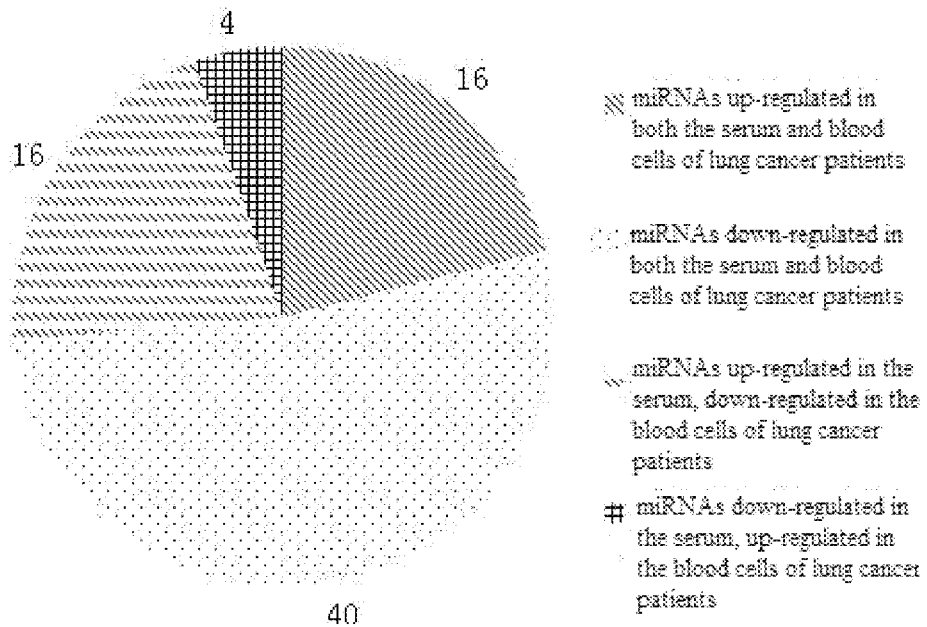
FIG. 1A shows the comparison on the tumor-specific miRNAs expressions in serum and blood cells between non-small-cell lung cancer patients and normal subjects.

Analysis on the results of Solexa sequencing shows that, compared with normal subjects, non-small-cell lung cancer patients have 16 tumor-specific miRNAs with down-regulated expression in blood cells and up-regulated expression in serum. See FIG. 1A.

The Solexa sequencing of serum and tissues comprises the following steps:
(1) collecting colon tissues and serum of normal subjects and colorectal cancer patients;
(2) extracting total RNA from the collected samples, extracting colon tissue RNAs for Solexa sequencing with Trizol reagent (Invitrogen Co.); the extraction of serum RNA for Solexa sequencing follows the same steps as adopted in the extraction of serum RNA for Solexa sequencing in the step of Solexa sequencing on serum and blood cells; and
(3) conducting Solexa sequencing with reference to the particular steps in the operation instructions by Illumine Co.

Figure 1B:
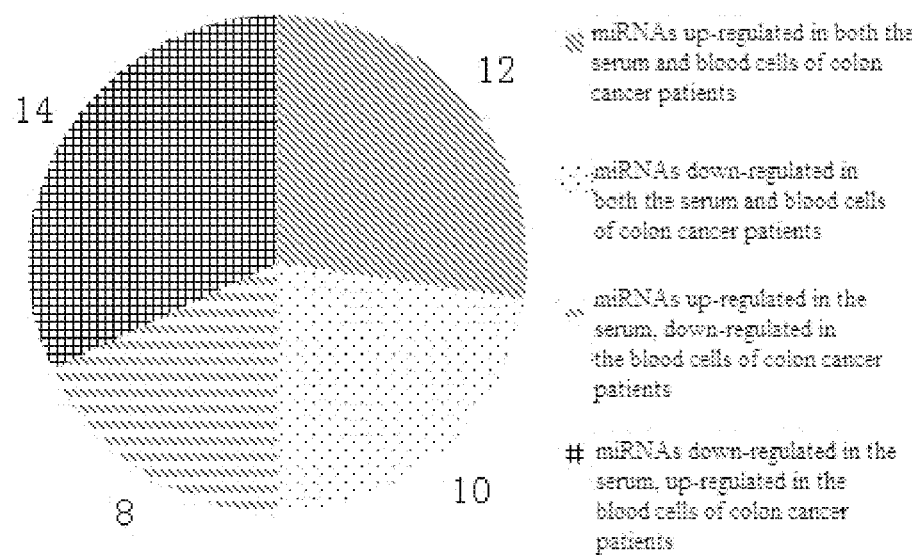
FIG. 1B shows the comparison on the tumor-specific miRNA expressions in serum and tissues between rectal cancer patients and normal subjects.

Analysis on the results of Solexa sequencing shows that, compared with normal subjects, colorectal cancer patients have 8 tumor-specific miRNAs with down-regulated expression in colon tissues and up-regulated expression in serum. See FIG. 1B.

In the above-mentioned two cancer cases, the expressions of tumor-specific miRNAs in tumor tissues/cells are different from those in serum (negatively correlated), indicating that miRNAs in serum are not only randomly released by broken cells in vivo, but also initiatively secreted by cells, reacting to the occurrence and progression of diseases. Therefore, it is indicated that the intervention of disease occurrence and progression can be achieved by modulating miRNA content in serum.

Example 2 Separation of and Observation on the Cellular MVs in Serum/Plasma And Cell Culture Medium The following techniques are applied in the separation of the cellular MVs in serum/plasma and cell culture medium:
(1) fractional centrifugation: first, centrifuging the serum/plasma or cultured cell samples successively at 300 g, 1500 g and 10000 g to remove all cells and debris; conducting ultra-centrifugation the supernatant (110000 g/) for 70 minutes, and collecting the sediment, or, the total cellular MVs of the serum/plasma or cell samples;
(2) immuno-adsorption: absorbing the cell-specific antibodies on tissue culture plates; or, incubating the pure serum/plasma with all the cells and debris removed or the cell culture medium directly with immuno-magnetic beads or in the culture plates (for 30 minutes or 1 hour); the cellular MVs can be absorbed and collected directly; and
(3) filtration: adding the serum/plasma or cultured cell samples with all the cells and debris removed into a concentrating centrifugation tube with filter membranes of 100 kD, and conducting centrifugation at 4,000 rpm; collecting the cellular MVs concentrated in the centrifuge tube.

The collected cellular MVs are observed by separation under transmission electron microscopy (FEI Tecnai T20 Transmission Electron Microscope). The preparation and observation of cellular MV electron microscopy samples include the following steps: fixing the cellular MV sediment with 2.5% of glutaraldehyde stationary liquid at 4° C. overnight; washing the sediment with PBS for 3 times, each time for 10 minutes; fixing the washed sediment at the room temperature for 60 minutes with 1% of osmic anhydride; embedding the fixed sediment in 10% gelatin, and then fixing the gelatin with glutaraldehyde at 4° C., cutting the fixed gelatin into small cubes (each cube smaller than 1 $mm^3$); dehydrating the cubes with ethylalcohol solutions of increasing concentration successively (30%, 50%, 70%, 90%, 95% and 100%×3); soaking the dehydrated cubes with epoxy resin and slicing up with Leica UC6 microtome; observing the slices under 120 kV Transmission Electron Microscopy.

Figure 2:
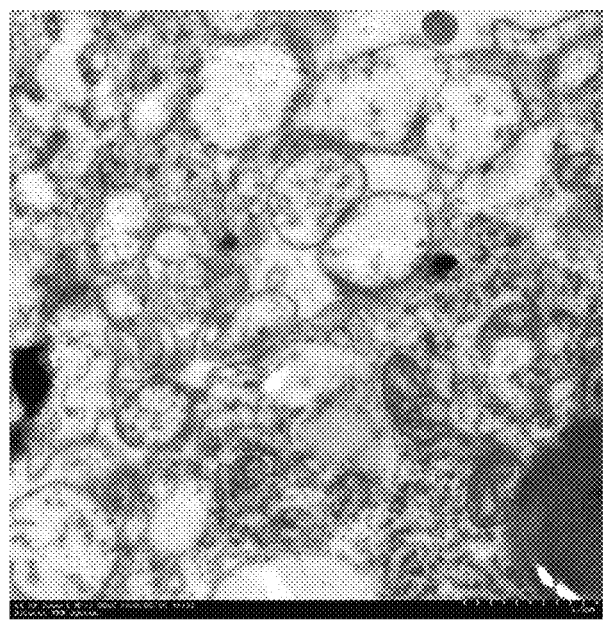
FIG. 2 shows the transmission electron microscopy image of cellular MVs in the serum/plasma of normal subjects.

The image of cellular MVs collected by fractional centrifugation under Transmission Electron Microscopy is shown in FIG. 2 that the cellular MVs separated from the serum/plasma of normal subjects vary in diameter, ranging between 10-500 nm.

Figure 3:
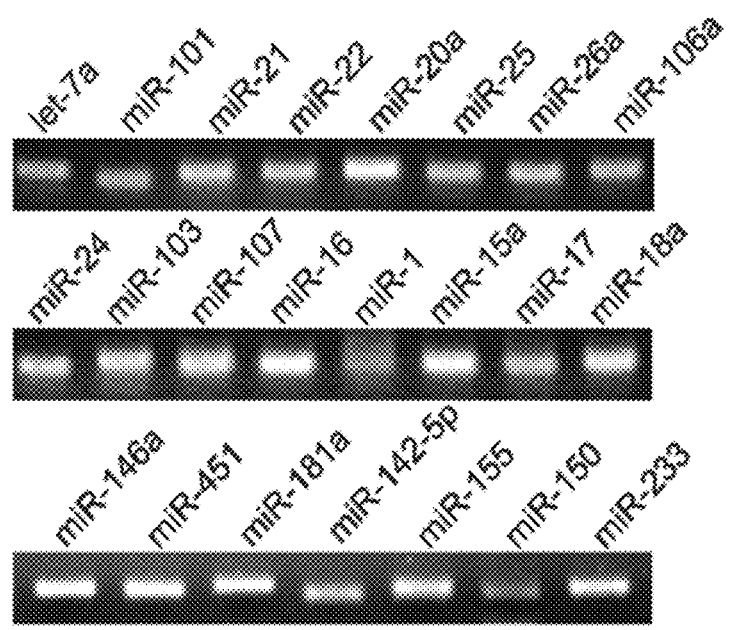
FIG. 3 shows the results of gel electrophoresis experiment on cellular MV-entrapped miRNAs in the serum of normal subjects.

Example 3: RT-PCR Experiment on the Cellular MV-Entrapped MiRNAs in Serum/Plasma In this example, it is discovered and proved with RT-PCR technique that the cellular MVs in human serum/plasma entrap various miRNAs with significantly different expression level. The specific experiment steps include:
(1) collecting the serum/plasma of normal subjects;
(2) separating the cellular MVs in the serum/plasma with the ultra-centrifugation method as applied in example 2;
(3) isolating and preparing cDNA samples; extracting total RNA of cellular MVs with Trizol reagent (Invitrogen Co.); converting the total RNA into the cDNA samples by RNA reverse transcription reaction. The reverse transcription reaction system comprises 4 μl of 5×AMV buffer, 2 μl of 10 mM each dNTP mixtures (Takara Co.), 0.5 μl of RNase Inhibitor (Takara Co.), 2 μl of AMV (Takara Co.) and 1.5 μl of mixture of specific reverse primers of the miRNAs for detection. The reaction steps are: incubating at 16° C. for 15 minutes, reacting at 42° C. for 1 hour, and then incubating at 85° C. for 5 minutes;
(4) PCR reaction: diluting the cDNA in the ratio of 1/50; adding 0.3 μl Taq (Takara Co.), 0.25 μl 10 μM of forward primer, 0.25 μl 10 μM of general reverse primer, 1.2 μl 25 mM of $MgCl_2$, 1.6 μl 2.5 mM of each dNTP mixture (Takara Co.), 2 μl of 10×PCR buffer, and 13.4 μl of $H_2O$ into 1 μl of diluted cDNA, and so a 20 μl system conducts PCR. PCR reaction conditions are: 95° C., 5 minutes for 1 cycle→95° C., 15 seconds; 60° C., 1 minute for 30 cycles; and
(5) electrophoresis observation: conducting electrophoresis on 10 μl PCR product on 3% of agarose gel. The gel is EB-stained and observed under a UV-lamp. FIG. 3 shows the RT-PCR experiment results on the total cellular MVs separated by ultra-centrifugation from the serum of normal subjects; the mature human miRNAs, over 500 kinds in total, are adopted for the PCR reaction; among them, 23 miRNAs are shown in FIG. 3 and known as let-7a, miR-101, miR-21, miR-22, miR-20a, miR-25, miR-26a, miR-106a, miR-24, miR-103, miR-107, miR-16, miR-1, miR-15a, miR-17, miR-18a, miR-146a, miR-451, miR-181a, miR-142-3p, miR-155, miR-150 and miR-233. Wherein, miR-150, miR-21, miR-142-5p and miR-181a are blood cell-specific, and let-7a is enriched miRNA in blood cells.

The results above-mentioned proves that the cellular MVs indeed entrap miRNAs, and the quantities of various miRNAs are different.

Example 4: Real-Time PCR Experiment on the Cellular MV-Entrapped miRNAs in Serum/Plasma in Different Physiological Statuses This example discovers and proves with the Real-time PCR technique that the miRNA expression level of the serum/plasma cellular MVs of atherosclerosis patients is different from that of normal subjects. The specific experiment steps are as follows:
(1) collecting whole blood (anti-coagulated) from normal subjects and atherosclerosis patients;
(2) separating the cellular MVs from serum/plasma with the differential centrifugation method as applied in example 2;
(3) isolating and preparing the cDNA samples with the method as applied in example 3;
(4) Real-time PCR reaction: conducting Real-time PCR validation on the expression variation of cellular MV-entrapped miRNAs in the serum/plasma of normal subjects and atherosclerosis patients on the serum/plasma cellular MV miRNAs with high expression quantities: miR-125b, miR-16, miR-451, miR-142-3p and miR-150. The cDNA is diluted in 1:50. 0.3 μl of Taq (Takara Co.); 0.25 μl of 10 μM forward primer, 0.25 μl of 10 μM general reverse primer, 1.41 of 25 mM $MgCl_2$, 1.6 μl of 2.5 mM each dNTP mixture (Takara Co.), 2 μl of 10×PCR buffer, and 12.4 μl of $H_2O$ are added into 1 μl of the diluted cDNA, and so a 20 μl system conducts the reaction. PCR reaction conditions are: 95° C., 5 minutes for 1 cycle→95° C., 15 seconds; 60° C., 1 minute for 40 cycles; and
(5) data analysis: treating the experiment data with the ΔCT method. ΔCT is set as the number of cycles when the reaction reaches the threshold value, and the comparison of the miRNAs in the two sample groups can be expressed with the equation $2^{-\Delta CT}$, in which $\Delta C_T = C_{Tgroup1} - C_{Tgroup2}$.

Figure 4:
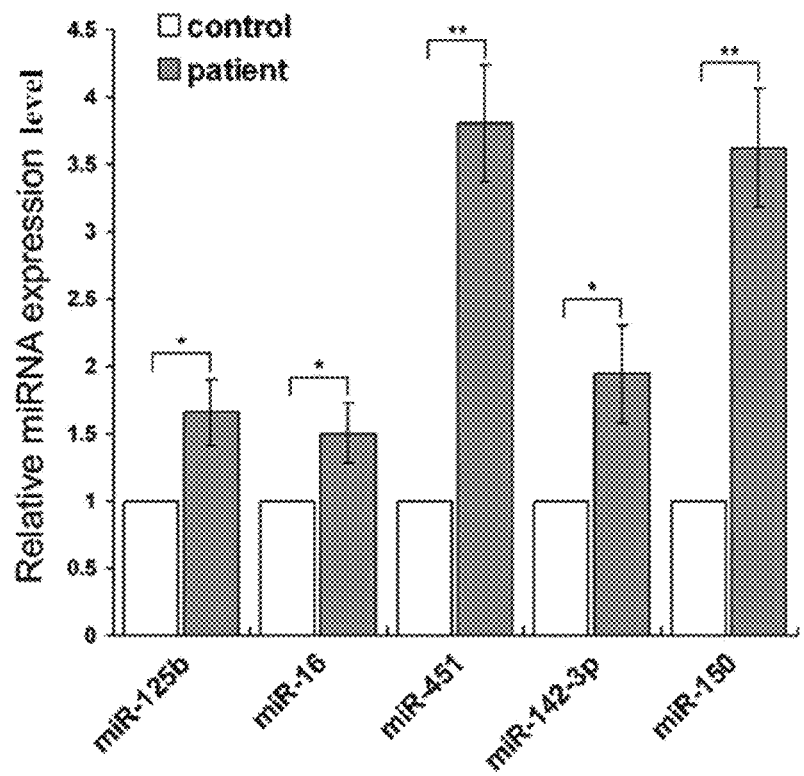
FIG. 4 shows the comparison on the cellular MV-entrapped miRNA expressions between atherosclerotic patients and normal subjects.

The detailed experiment results are shown in FIG. 4 that there is significant difference in the expression level of certain miRNAs such as miR-125b, miR-16, miR-142-3p, especially miR-451 and miR-150 entrapped in the serum/plasma cellular MVs of normal subjects and atherosclerosis patients. The expression variations of cellular MV-entrapped miRNAs between morbid condition and normal condition indicate that the cellular MV-entrapped miRNAs are related to diseases, and that the variations of miRNAs are probably the cause of diseases, because the disease inhibitory and enhancing factors may be the targets of miRNAs, when there is miRNA expression disorder, for example, down-regulation of miRNAs that inhibit disease enhancing factors or up-regulation of miRNAs that inhibit the disease inhibitory factors will cause a series of down-stream gene expression alteration and pathway disorder, and then cause diseases; conversely, up-regulation of miRNAs that inhibit the disease enhancing factors or down-regulation of miRNAs that inhibit the disease inhibitory factors will cause down-regulation of a series of down-stream disease enhancing genes, and inhibit disease occurrence or progression. Therefore, miRNAs can be regarded as drug targets. Disease occurrence and progression shall be considerably inhibited by inhibiting the up-regulated miRNAs and over-expressing down-regulated miRNAs. The experiment indicates that the prevention/treatment of disease can be achieved by modulating the cellular MV-entrapped miRNAs content.

Example 5: Modulation of Cellular MV-Entrapped MiRNA Content by the Introduction of Stimulants This example proves that, after the introduction of stimulants into the blood of normal subjects, the content of miRNA secreted by MVs in blood cell is varied.

The specific steps are as follows:
(1) collecting the whole blood (anti-coagulated) of human beings; dividing the whole blood into two average samples; adding 100 ng/ml of lipopolysaccharide (LPS) into one sample and incubating it at 37° C. for 1 hour; no LPS is added into the other sample, which is used as the control;
(2) conducting differential centrifugation as applied in example 2 on the two whole blood samples, and the cellular MVs treated with LPS and the cellular MVs not treated with LPS (the control subject) are produced;
(3) preparing cDNA samples with reference to the method as applied in example 3;
(4) conducting the Real-time PCR reaction with reference to the method as applied in example 4; and
(5) analyzing data with reference to the method as applied in example 4.

Figure 5A:
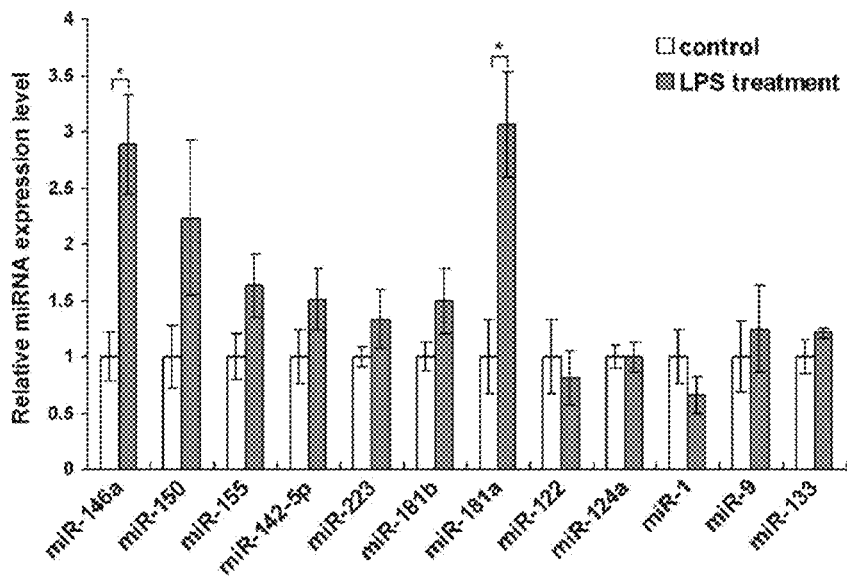
FIG. 5A shows the comparison between the expressions of cellular MV-entrapped miRNAs in the whole blood of normal subjects treated and in those untreated by LPS.

The data analysis results are shown in FIG. 5A that, after treatment, some of the cellular MV miRNAs in the whole blood of normal subjects are up-regulated, wherein the miRNAs that are immune related are more obvious, such as miR-181a, miR-146a and miR-150, and etc.

Besides, this example also demonstrates that other stimulants can cause variation of the miRNAs content entrapped in the cellular MVs secreted by the incubated cells.

The specific experiment steps are as follows:
(1) taking the monocytic series/macrophage system THP-1 that plays an important role in inflammatory reaction as the research subject; incubating the THP-1 cells in the RPMI 1640 culture medium (Gibco, USA) added with 10% of fetal bovine serum (Gibco, USA), in a 5% of $CO_2$ atmosphere and at 37° C.; free fatty acid (FFAs, with the final concentration of 4000μ), advanced glycosylation end product (AGEs, with the final concentration of 100 μg/mL) and $H_2O_2$ (with the final concentration of 10004) are used as stimulants to THP-1, and the cells treated with BSA are the control;
(2) centrifuging the incubated cells at 1,000 rpm and collecting the cell pellets; conducting the supernatant by the differential centrifugation as applied in example 3 so that the cellular MVs are separated;
(3) preparing cDNA samples reference to the method as applied in example 3;
(4) conducting the Real-time PCR reaction with the method as applied in example 4, taking miR-16 as the standard subject and draw the standard curve; and
(5) determining the absolute expression quantities of all miRNAs by comparing with the standard curve and conducting the statistical analysis.

Figure 5B:
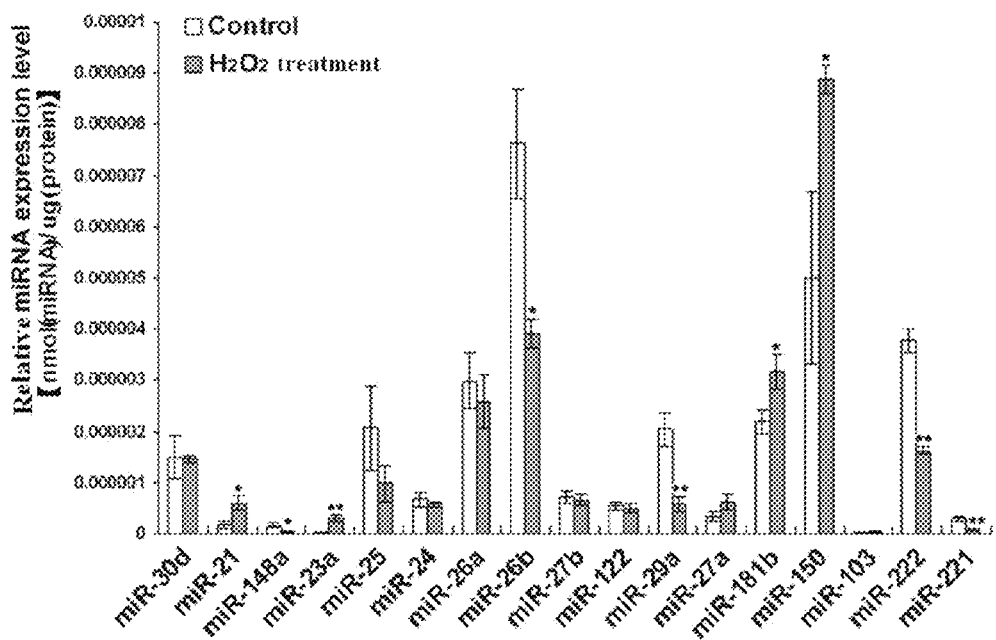
FIG. 5B shows the comparison between the expressions of cellular MV-entrapped miRNAs in the THP-1 cell treated and in those untreated by $H_2O_2$.
Figure 5C:
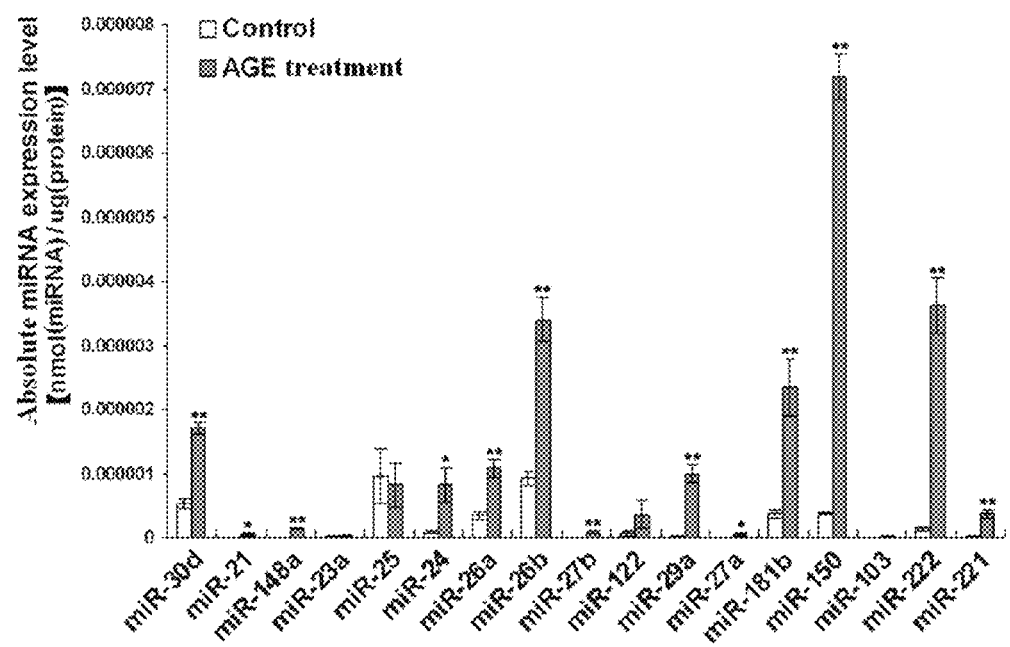
FIG. 5C shows the comparison between the expressions of cellular MV-entrapped miRNAs in the THP-1 cell treated and in those untreated by AGE.
Figure 5D:
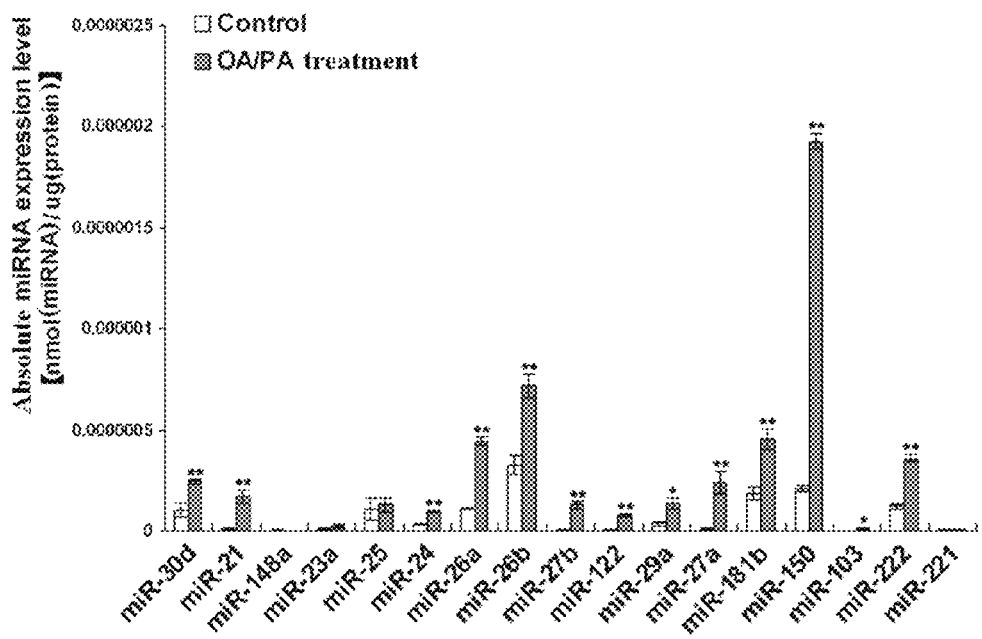
FIG. 5D shows the comparison between the expressions of cellular MV-entrapped miRNAs in the THP-1 cell treated and in those untreated by FFAs.

The analysis results are shown in FIG. 5B-D that being treated with FFAs (that is, oleic acid (OA) and palmic acid (PA), FIG. 5D), AGEs (FIG. 5C) and $H_2O_2$ (FIG. 5B), the cellular MV miRNA content is completely different from that before the treatment. For example, being treated with $H_2O_2$, the expression level of cellular MV miRNAs, such as miR-26a, miR-29a and miR-222, drops sharply, while the expression level of miR-150 and miR-181b is up-regulated. It is indicated that the cellular MV-entrapped miRNA content can vary by the introduction of stimulants.

Example 6: Modulating the Cellular MV-Entrapped miRNA Content by the Introduction of Pre-MiRNAs and Antisense RNAs In this example, the level of cellular MV-entrapped miR-150 is up-regulated by artificially introducing the pre-miR-NAs of miR-150 in vitro.

The experiment steps are as follows:
Firstly, transfecting the pre-miRNAs into THP-1 cells with liposome (invitrogen Co., Lipofectamine 2000). The specific steps are as follows:
(1) incubating the THP-1 cells in the RPMI 1640 culture medium (Gibco, USA) added with 10% of fetal bovine serum (Gibco, USA), in a 5% of $CO_2$ atmosphere and at 37° C.;
(2) adding 30 μl of lipofectamine 2000 and 600 pmol of negative control pre-RNA into 1 ml of OPTI-MEM culture medium (Gibco, USA) respectively to form mixtures A and B, which are placed at the room temperature for 5 min;
(3) adding 30 μl of lipofectamine 2000 and 600 pmol of pre-miR-150 into 1 ml of OPTI-MEM culture medium (Gibco, USA) respectively to form mixtures C and D, which are placed at the room temperature for 5 min;
(4) mixing mixtures A and B to form mixture E, which is placed for 20 min;
(5) mixing mixtures C and D to form mixture F, which is placed for 20 min;
(6) adding mixture E and F into the cells of the control group and the experimental group respectively, and the OPTI-MEM culture medium is replenished to 15 ml; the culture is conducted in a 5% of $CO_2$ atmosphere and at 37° C.;
(7) replacing the culture medium with normal nutrient solution after 6 hours; and
(8) the transfection finishes after 24-48 hours; collecting the cells, and separating and preparing the cellular MVs introduced with pre-miR-150 with the method to separate and prepare miRNAs as applied in example 2.

Secondly, to detect the cellular MV-entrapped miR-150 content with the Real-time PCR technique as applied in example 4.

Figure 6A:
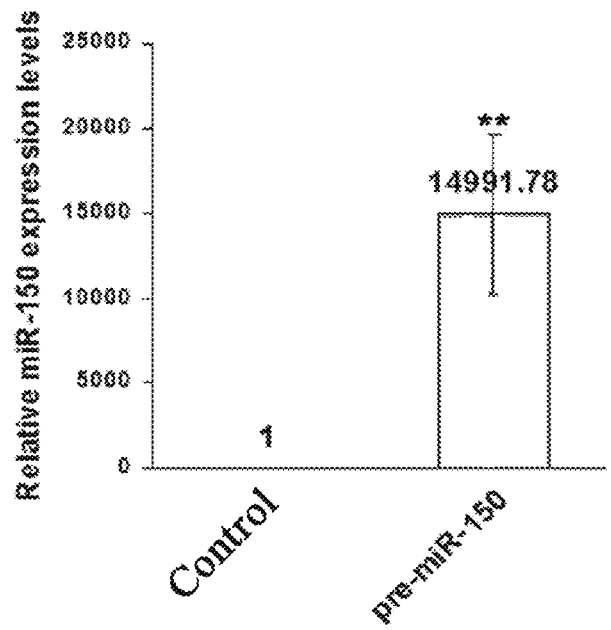
FIG. 6A shows the content results of up-regulating the quantity of miRNA in cellular MVs by introducing miRNA precursors.

The detection results are shown in FIG. 6A that, after transfection, the cellular MV-entrapped miR-150 expression is up-regulated significantly. It is indicated that certain miRNA expression level can be up-regulated by the introduction of pre-miRNAs in vitro.

A method of down-regulating cellular MV miR-150 content by introducing miR-150 antisense RNA includes steps as follows: firstly, to transfect the miR-150 antisense RNAs into THP-1 cells with Lipofectamine 2000 (Invitrogen). The specific steps include:
(1) incubating THP-1 cells in the RPMI 1640 (Gibco, USA) added with 10% fetal bovine serum (Gibco, USA), cultured in a 5% of $CO_2$ atmosphere in a 5% of $CO_2$ atmosphere and at 37° C.;
(2) mixing 30 μl of lipofectamine 2000 and 600 pmol of negative control antisense RNA with 1 ml OPTI-MEM culture medium (Gibco, USA) respectively to form mixtures A and B, which are placed at the room temperature for 5 min;
(3) mixing 30 μl of lipofectamine 2000 and 600 pmol of miR-150 antisense RNA with 1 ml OPTI-MEM culture medium (Gibco, USA) respectively to form mixtures C and D, which are placed at the room temperature for 5 min;
(4) mixing mixtures A and B to form mixture E, which is placed for 20 min;
(5) mixing mixtures C and D to form mixture F, which is placed for 20 min;
(6) adding mixtures E and F into the control group and the experimental group respectively, replenishing the OPTI-MEM culture medium to 15 ml, and incubating the cells in a 5% $CO_2$ atmosphere and at 37° C.;
(7) replacing the culture medium with normal nutrient solution after 6 hours;
(8) the transfection finishes after 24-48 hours; collecting the cells, and separating and preparing the miRNAs with the method as applied in example 2.

Secondly, to detect the cellular MV miR-150 content reference to the Real time-PCR method as applied in example 4.

Figure 6B:
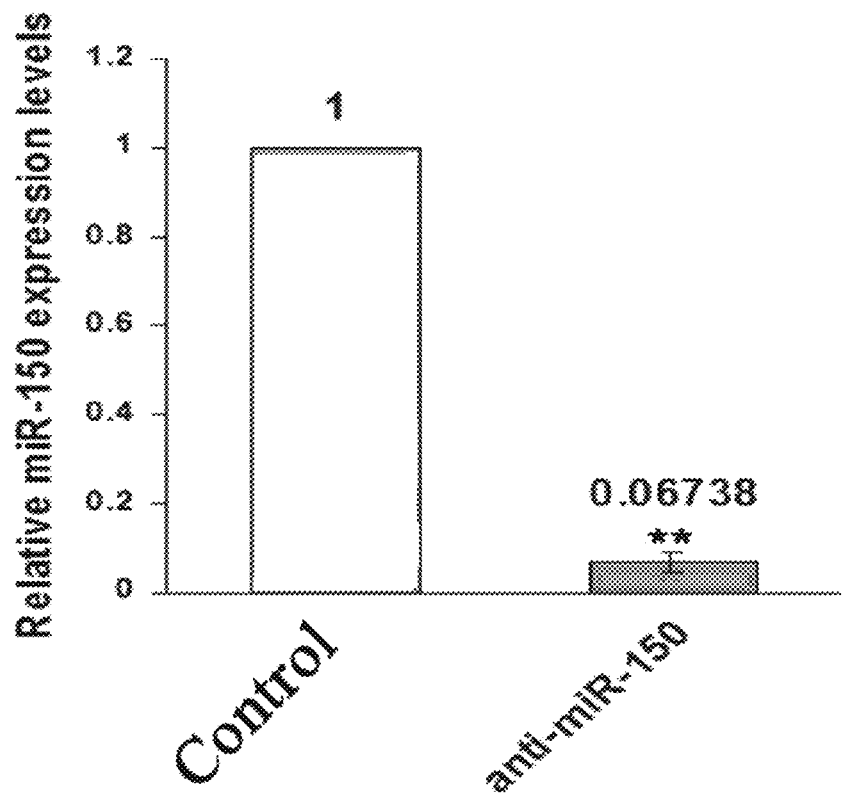
FIG. 6B shows the content result of down-regulating the quantity of miRNAs in cellular MVs by introducing the antisense RNAs of miRNAs.

The results are shown in FIG. 6B that the expression level of transfected cellular MV-entrapped miR-150 is down-regulated significantly; it is indicated that certain miRNA content can be reduced by introducing its antisense RNA in vitro.

Example 7: Interaction Between Cellular MVs, Cellular MV-Entrapped miRNAs and Target Cells This example discovers and proves by the confocal microscope technique, the Real-time PCR technique, the western blot technique and the cell migration experiment technique that the cellular MV-entrapped miRNAs can be delivered effectively in a targeted way between non-adjacent cells and will affect targeted cell functions to some certain extent.

Firstly, conducting fluorescent labeling on the THP-1 cells with dyer diI-$C_{16}$ (1 h, 37° C.), stimulating the THP-1 cells with AGEs (6 h, 37° C.), then separating the cellular MVs secreted by the THP-1 cells by centrifugation.

Figure 7A:
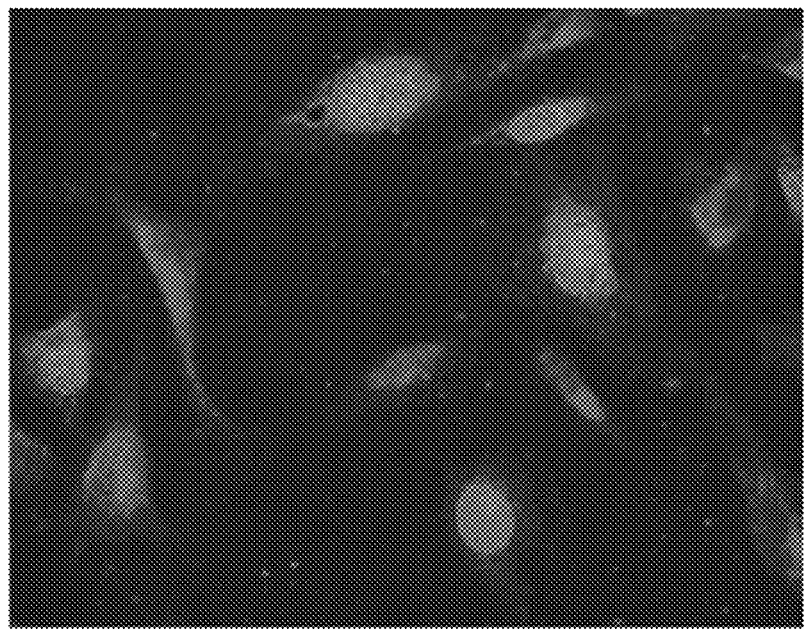
FIG. 7A shows the specificity interactions between THP-1 cellular MVs and HMEC-1 cells.

Adding the cellular MVs secreted by the THP-1 cells into human microvascular endothelial cells (HMEC-1) and incubating them at 37° C. for 6 h. The HMEC-1 cells were incubated in MCDB-131 culture medium added with 10 ng/ml of epidermal growth factor (Becton-Dickinson, USA), 10 ng/ml of hydrocortisone (Sigma) and 10% of fetal bovine serum (Gibco, USA), in a 5% of $CO_2$ atmosphere and at 37° C. The cells are observed with the confocal microscope (FV1000, Olympus). The results are drawn in FIG. 7A, wherein the blue part is the stained nucleoli of HMEC-1 cells. It can be seen from FIG. 7A that the cellular MVs secreted by THP-1 cells can enter the HMEC-1 cells and performing specific interaction with the HMEC-1 cells.

Figure 7B:
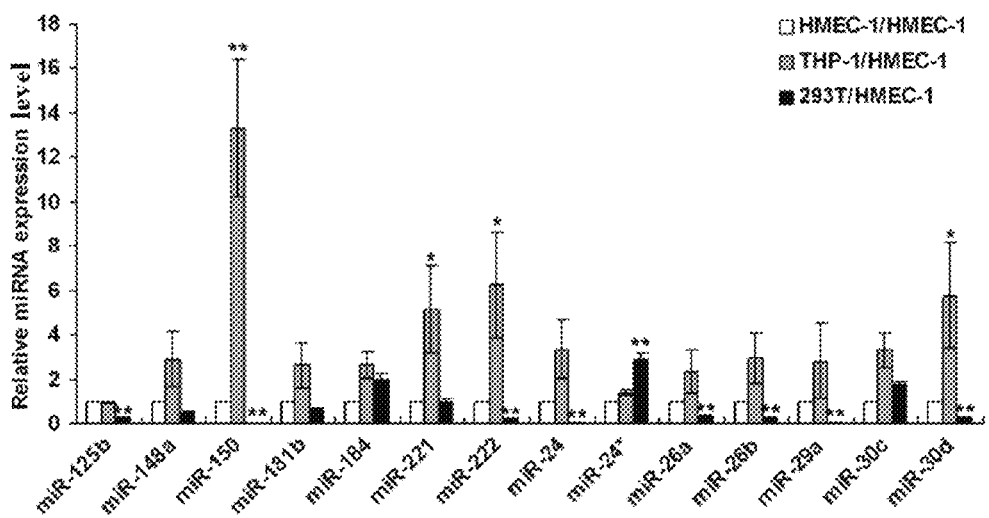
FIG. 7B shows the expression levels of miRNAs in HMEC-1 cells, THP-1 cells and 293T cells.

Secondly, the cellular MV-entrapped miRNAs can up-regulate the quantity of the related miRNAs such as miR-150 in the targeted cell. The specific experiment steps are:

(1) selecting the expression profile of THP-1, 293T and HMEC-1 cells, and the selection results are shown in FIG. 7B. The expression level of each miRNA in the THP-1 cells is different from that of HMEC-1 cells, especially miR-150, whose expression quantity in THP-1 cells is much higher than that in HMEC-1 cells. Therefore, miR-150 is chosen as the subject for the research on the interaction between cellular MV-entrapped miRNAs and their target cells.

(2) stimulating the THP-1 and 293T cells with 100 μg/ml AGEs;

(3) separating the cellular MVs from the THP-1 and 293T cells respectively with the differential centrifugation method as applied in example 2;

(4) incubating the cellular MVs separated from the THP-1 and 293T cells respectively with HMEC-1 cells at 37° C. for 6 hours;

(5) extracting respectively total RNA from the HMEC-1 cells that are not treated with cellular MVs and the HMEC-1 cells that are incubated with the cellular MVs separated from the THP-1 and 293T cells, and preparing cDNA samples reference to the method as applied in example 3;

(6) conducting the Real-time PCR reaction reference to the method as applied in example 4; and (7) conducting data analysis reference to the method as applied in example 4.

Figure 7C:
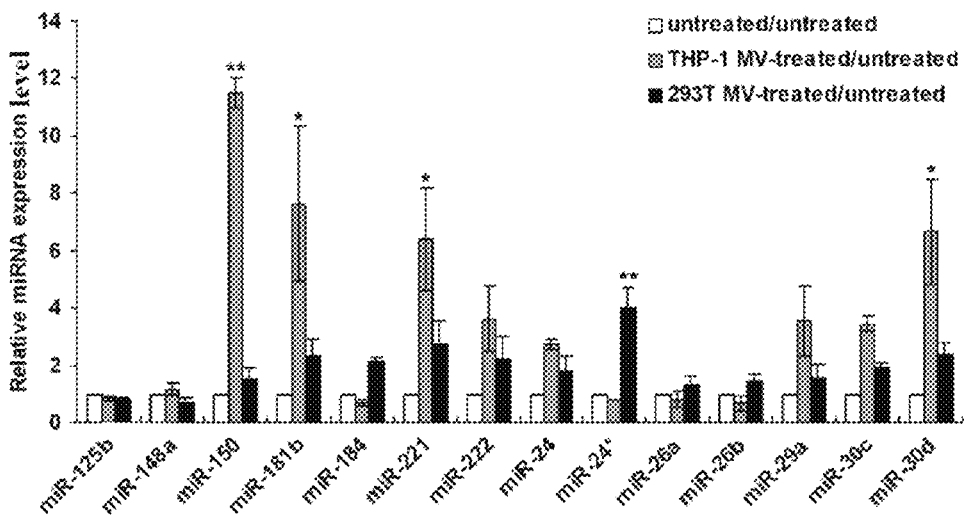
FIG. 7C shows the expression levels of miRNAs in HMEC-1 cells, THP-1 cells treated by AGEs, and HMEC-1 cells incubated with 293T cellular MVs.

The data analysis results are shown in FIG. 7C that the cellular MVs separated from the THP-1 cells with miR-150 high expression is high can up-regulate the miR-150 expression in the HMEC-1 cells with miR-150 low-expression to more than 10 times, and the cellular MVs separated from the HMEC-1 cells with miR-150 low expression cannot up-regulate the miR-150 expression in the HMEC-1 cells. It is indicated that the miR-150 expression in the HMEC-1 cells is up-regulated by the abundant miR-150s entrapped in the cellular MVs of THP-1 cells, instead of the endogenous up-regulation caused by the introduction of cellular MVs.

Figure 7D:
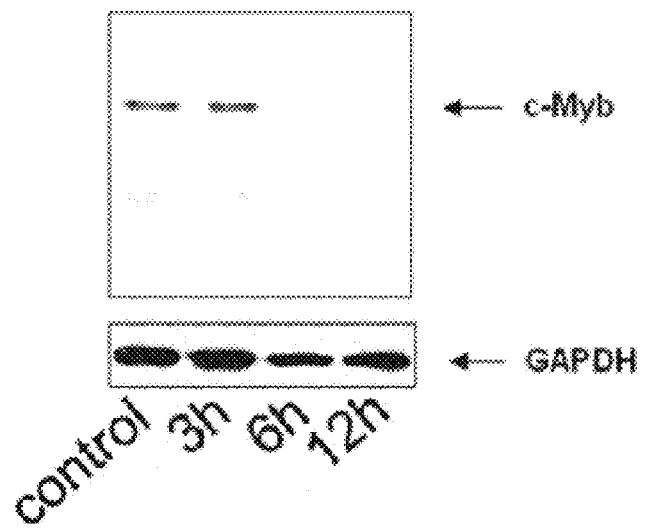
FIG. 7D shows the results of western blot detection on c-Myb proteins in HMEC-1 cell introduced with THP-1 cellular MVs.

Thirdly, the miR-150s introduced to HMEC-1 cells through cellular MVs can down-regulate the expression of the target protein c-Myb, so that the migration capability of HMEC-1 cells is promoted. The specific experiment steps include:

(1) stimulating THP-1 cells with 100 μg/ml AGEs;

(2) separating the cellular MVs of THP-1 cells reference to the differential centrifugation method as applied in example 2;

(3) adding the THP-1 MVs into HMEC-1, and incubating at 37° C. for 3 h, 6 h, 12 h; and (4) extracting respectively the total protein for western blot detection with the total protein of HMEC-1 cells without being incubated with THP-1 cell MVs as the control, and GAPDH as the internal reference. The detection results are shown in FIG. 7D that the c-Myb protein of HMEC-1 cells introduced with THP-1 cell MVs is obviously down-regulated. Due to that miRNAs function mainly through blocking the translation treat of their target DNAs, the c-Myb protein quantity variation can indirectly prove the effect of the cellular MV-entrapped miR-150s in target cells.

Figure 7E:
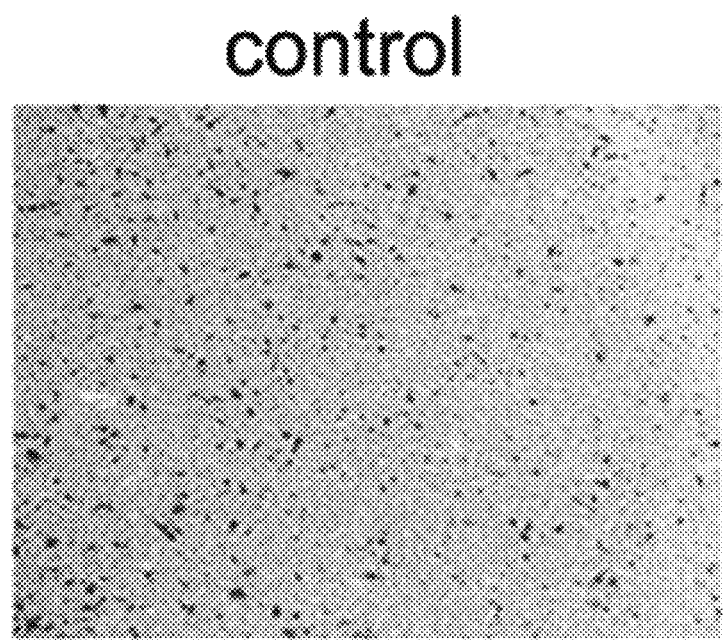
FIGS. 7E and 7F are respectively photos of the migration of HMEC-1 cells untreated and those treated by THP-1 cellular MVs.
Figure 7F:
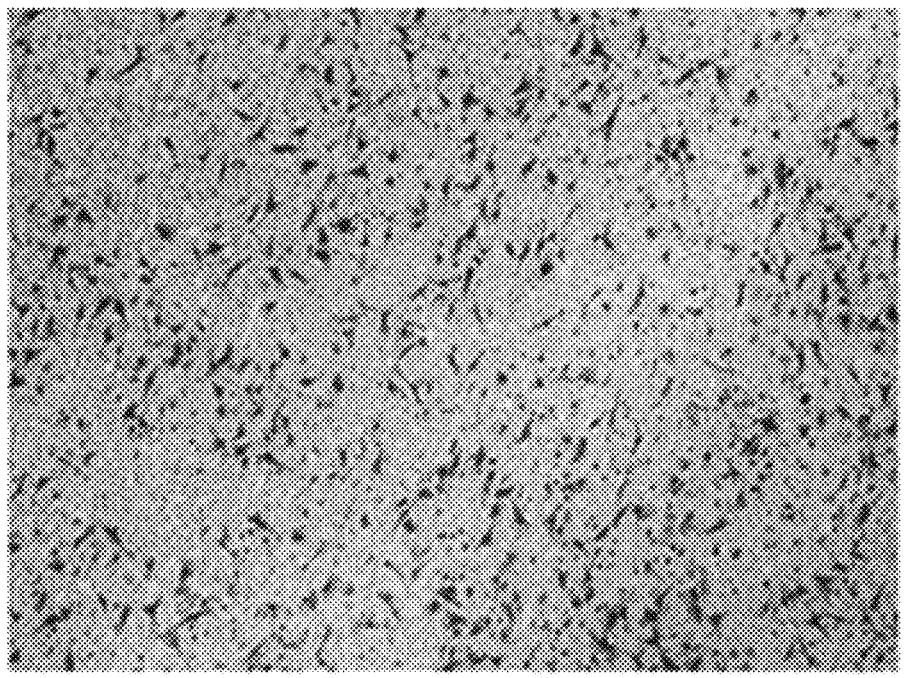
Figure 7G:
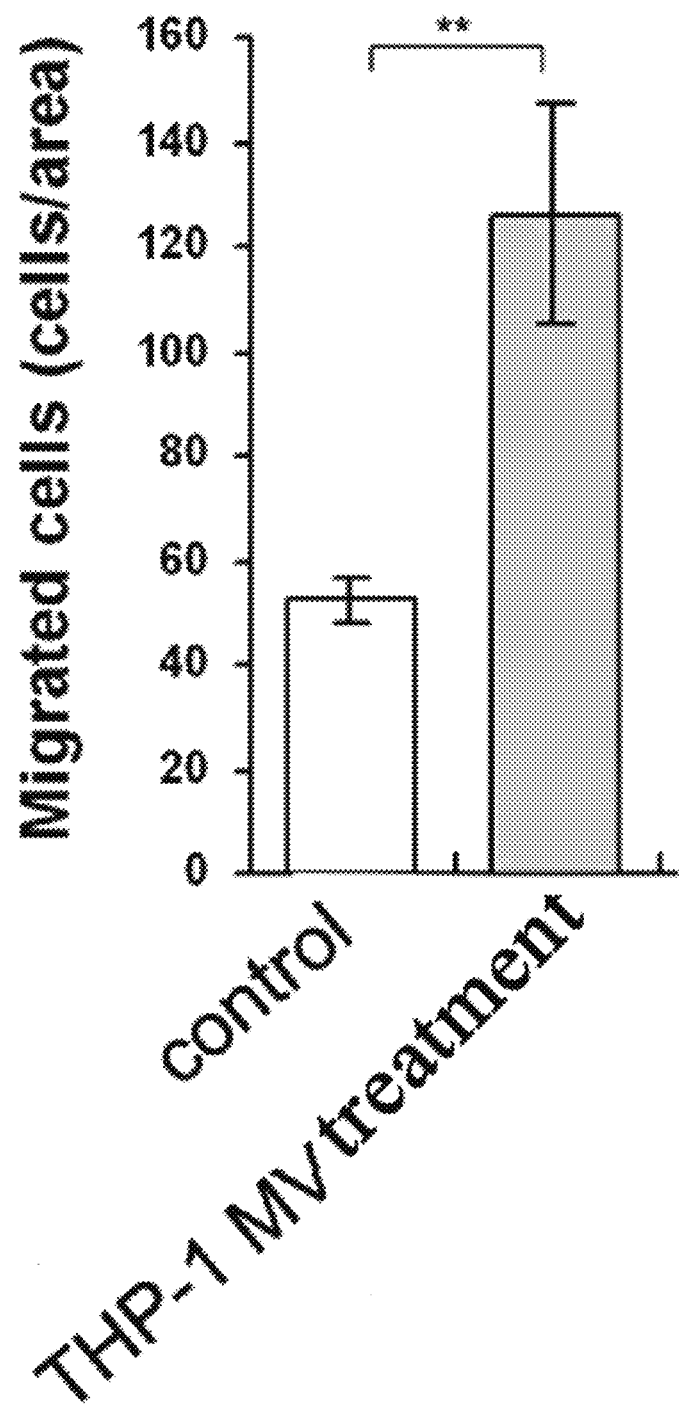
FIG. 7G shows the migrated cell counting results of HMEC-1 cells untreated and treated THP-1 cellular MVs.

Due to the important role the c-Myb proteins play in cell multiplication, differentiation and migrate, the migration capability variations of HMEC-1 cells incubated with THP-1 cell MVs are also detected. The specific experiment steps include:

(1) covering the polycarbonate membrane (8 μm aperture) at the bottom of the upper chamber of the Transwell chambers (Transwell Boyden Chamber, 6.5 mm, Costar, Cambridge, Mass., USA) with 0.1% of glutin;

(2) suspending the HMEC-1 cells with the nutrient medium that contains no serum, and control the concentration in $(1-10) \times 10^5$/ml; incubating the HMEC-1 cells with the THP-1 cell MVs for 2 h, with the cells without being incubated with the THP-1 cell MVs as control; and then adding the HMEC-1 cells into the upper chamber, and add 0.5 ml of nutrient medium that contains 10% of fetal bovine serum into the lower chamber; incubating in the cell incubator in a 5% of $CO_2$ atmosphere for 4 h; and (3) immobilizing the cells that have migrated to the lower chamber with 90% of ethanol for 15 min at the room temperature, then washing the cells and staining them with 0.1% of crystal violet for 15 min at the room temperature; scraping the cells from the filtration membrane and taking photos (Olympus, BX51, Japan); the photos are shown in FIG. 7E (without incubation with THP-1 cell MVs, the control) and FIG. 7F (incubated with THP-1 cell MVs); counting the number of cells in the 5 fields selected randomly under the microscope, and the results are shown in FIG. 7G; the photos and counting results prove that, due to the down-regulation of c-Myb proteins, the migration capability of the HMEC-1 cells treated with the THP-1 cell MVs improves obviously.

The results of the above-mentioned experiments show that various cells can secret miRNAs to cellular MVs, which deliver the miRNAs to recipient cells, and then the miRNAs function in the recipient cells. It is indicated that the cellular MV-entrapped miRNAs can be used as drugs, which can be delivered highly compatibly and specifically to the target cells with cellular MVs and then achieve drug prophylaxis/medication by affecting the target cell functions related to disease occurrence.

Besides, the THP-1 cellular MVs also deliver the other miRNAs, such as miR-136, miR-30c and miR-26a, to HMEC-1 cells. Meanwhile, miRNA exchange exists between the HMEC-1 and 293T cells. Therefore, besides the study on miR-150, study on the biological functions performed in the HMEC-1 cells by the other delivered THP-1 cell MV-entrapped miRNAs, and on the communication mechanism among the THP-1, HMEC-1 and 293T cells in various pathological and physiological statuses is also very interesting.

The example has also assessed the capability of the cellular MV-entrapped miRNAs to enter the target cells.

Figure 7H:
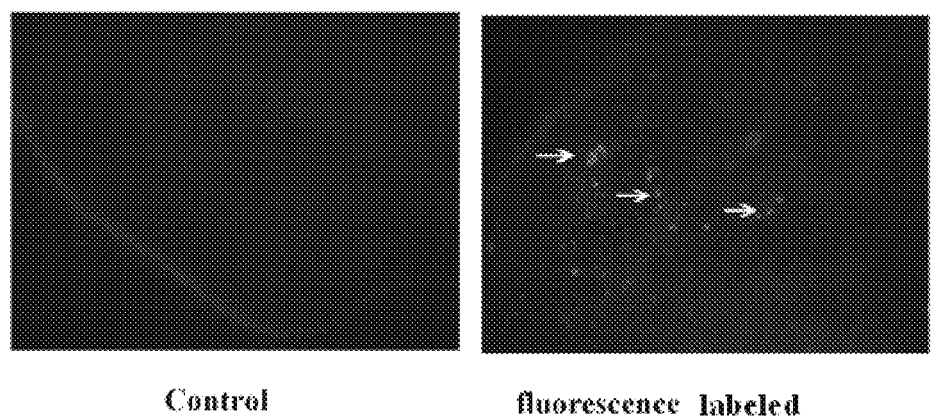
FIG. 7H shows the entrance of fluorescent labeled THP-1 cellular MVs into mouse vascular endothelial cell by the tail intravenous injection.

Firstly, the THP-1 cell MVs are labeled with fluorescent. The specific steps are: conducting the fluorescent labeling (red) on the THP-1 cells with dye diI-$C_{16}$ (1 h, 37° C.), and incubating the cells for 12 h; separating the fluorescent-labeled cellular MVs from THP-1 cells by centrifugal separation, and injecting intravenously into the C57BL/6 mouse; 6 h later, separating the vein endoderm of the mouse and observing under fluorescence microscope. The observation results are shown in FIG. 7H-1. Compared with the control that the vein endoderm of the mouse injected with cellular MVs without being fluorescent-labeled (FIG. 7H, left), the vein endoderm of the mouse injected with cellular MVs with being fluorescent-labeled (FIG. 7H, right) shows obvious fluorescent labels. It is proved that the cellular MVs can enter into the living beings by blood circulation and into target cells effectively.

Figure 7I:
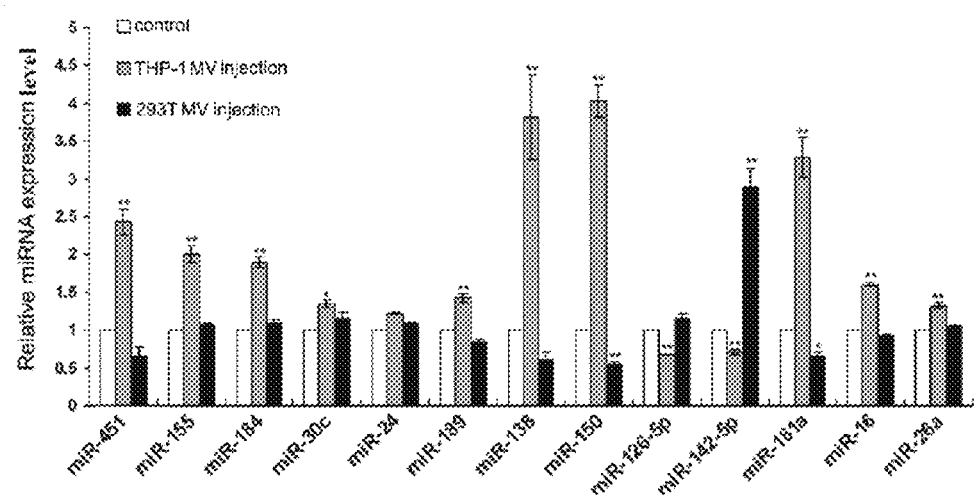
FIG. 7I shows the influence on the miRNA expression of C57BL/6 mouse from intravenous injection of THP-1 or 293T cellular MVs.

Meanwhile, the expression pattern and quantity of miRNAs in the mouse vascular tissue are detected with the Real-time PCR technique as applied in example 4. The detection results are shown in FIG. 7I that the expression quantities of miR-150, miR-138 and miR-181a are up-regulated 6 h after the mouse being injected with cellular MVs. It is indicated that the cellular MV-entrapped miRNAs can be delivered in vivo to target cells or tissues.

All the above experiment results prove that cellular MVs are an effective type of inter-cellular delivery medium. They can effectively and specifically deliver miRNAs amongst cells both in vivo and in vitro, so that the cell functions can be specifically affected with the miRNAs inhibiting the expression of their target genes. Therefore, the diseases can be prevented/treated to certain extent by inhibiting intentionally the expression of the genes involved in the disease occurrence and progression treat with the cellular MV-entrapped miRNAs; the miRNA entrapping-cellular MVs can be used as drugs to facilitate disease prevention/treatment.

Example 8: The Prevention & Treatment of the Diseases by Modulating miRNA Content in Cellular MVs This example accesses the effect on recipient cells from the donor cellular MV-entrapped miRNAs by modulating their content, so that it can be proved that the occurrence and progression of the diseases can be inhibited by modulating the content of cellular MV-entrapped miRNAs.

This example takes the macrophage and endothelial cells in the atherosclerosis status as study subjects, and studies the remission effect on the disease progression from cellular MVs entrapping miRNAs.

The types and numbers of cellular MVs increase in the chronic inflammation status, and the proliferation and migration of blood vessel endothelial cells is the main treat of atherosclerosis; therefore, it is studied in the first place that whether atherosclerosis patient serum/plasma cellular MV-entrapped miRNAs expression variations have happened to the cellular MV-entrapped miRNAs in the serum/plasma of atherosclerosis patients, and whether the migration capability of HMEC-1 cells can be promoted. To be specific, the experiment includes two parts as follows:

On one aspect, the expression level of miR-150 and the other miRNAs entrapped in the cellular MVs from the serum/plasma of normal subjects is compared with that of atherosclerosis patients. The specific steps include:
(1) separating respectively the cellular MVs from the serum/plasma of normal subjects and atherosclerosis patients with the differential centrifugation method as applied in example 2;
(2) preparing cDNA samples with reference to the method as applied in example 2;
(3) conducting the Real-time PCR reaction with reference to the method as applied in example 4; and
(4) analyzing data with reference to the method as applied in example 4.

As shown in FIG. 4, the data analysis results show that, compared with the cellular MVs in the serum/plasma of normal subjects, the cellular MVs in the serum/plasma of atherosclerosis patients show obvious up-regulation of miR-150 and miR-451.

Figure 8A:
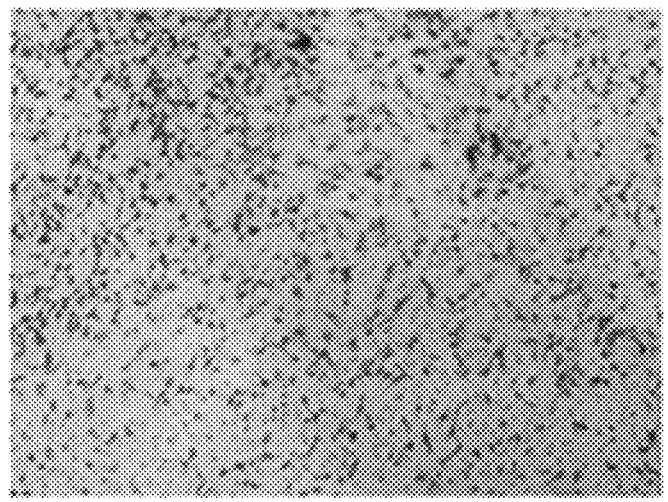
FIGS. 8A-C show the photos of the migration of HMEC-1 cells untreated and treated by serum/plasma cellular MVs from normal subjects and arteriosclerosis patients respectively.
Figure 8B:
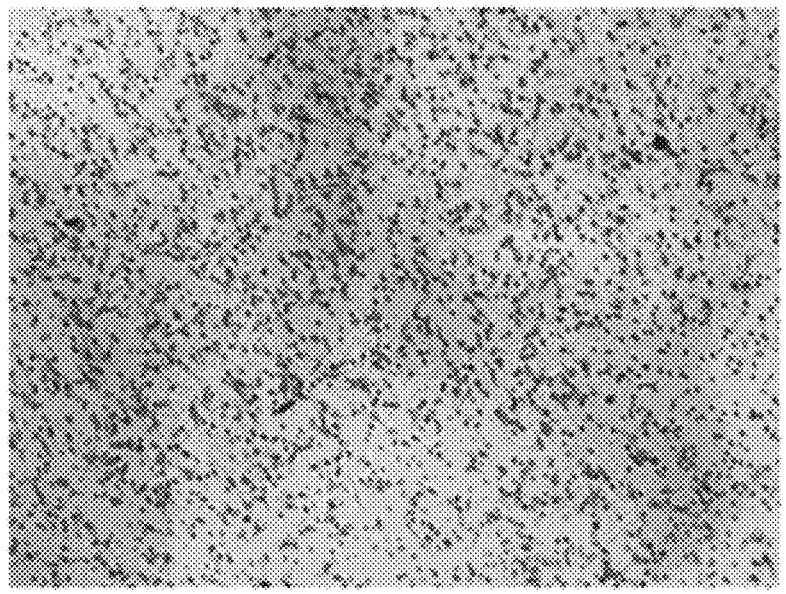
Figure 8C:
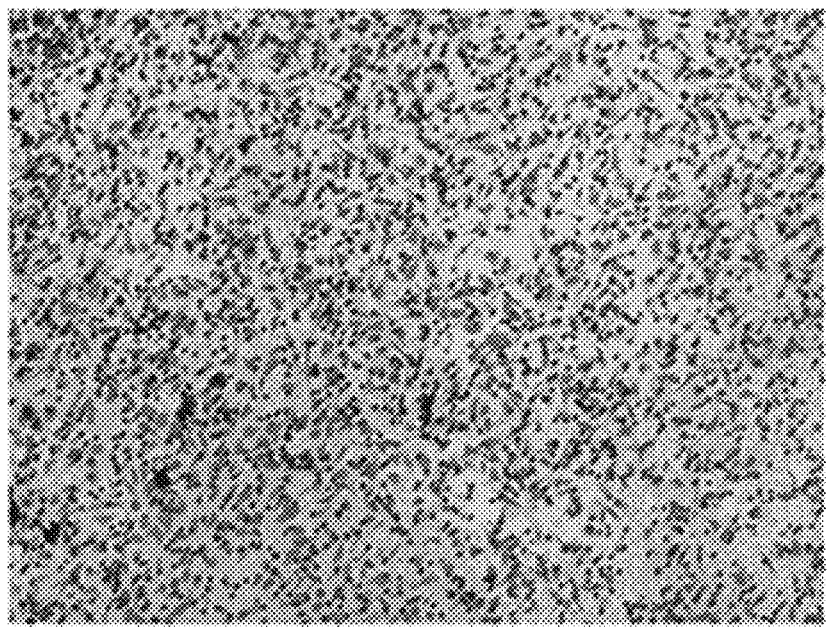
Figure 8D:
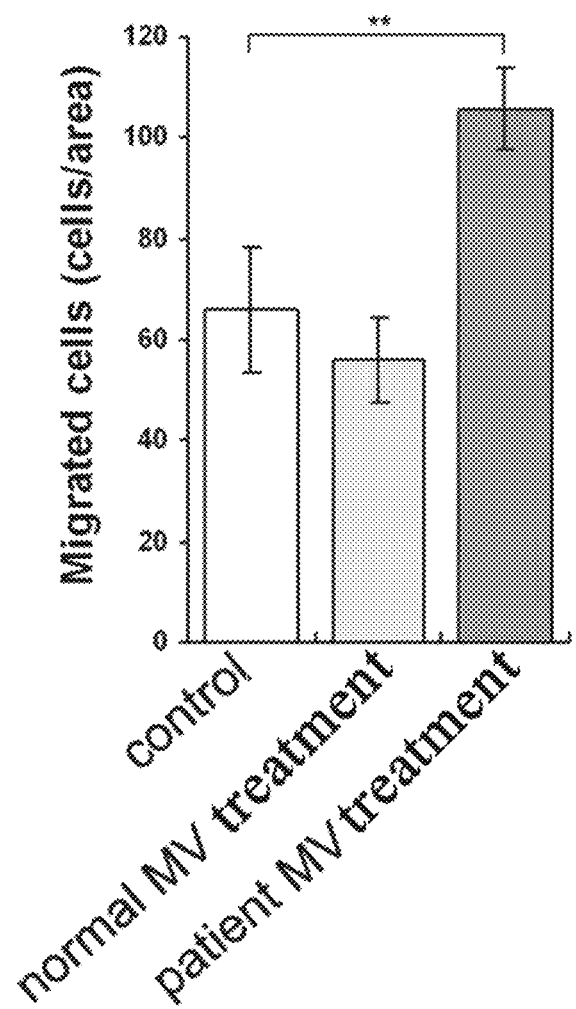
FIG. 8D shows the migration cell counting results of HMEC-1 cells untreated and treated by serum/plasma cellular MVs of normal subjects or arteriosclerosis patients.

On another aspect, the effect on the migration capability of HMEC-1 cells from the cellular MVs in the atherosclerosis patient serum/plasma is studied, with the HMEC-1 cells untreated with serum/plasma cellular MVs as the control. The results are shown in FIGS. 8A-8C. FIG. 8A is the photo-image of cell migration of the control (control), FIG. 8B is the photo-image of cell migration after being treated with the cellular MVs in the serum/plasma of normal subjects (THP-1 MV), and FIG. 8C is the photo-image of cell migration after being treated with the cellular MVs in the serum/plasma of atherosclerosis patients (293T MV). The migrated cells are counted and the migration rate is shown in FIG. 8D, which shows that, compared with the HMEC-1 cells untreated with cellular MVs, the HMEC-1 cells treated with the cellular MVs in the atherosclerosis patients' serum/plasma show obviously stronger migration capability; meanwhile, the cellular MVs in the normal subjects' serum/plasma have no effect on the migration capability of HMEC-1 cells.

The above results prove that, in various physiological and pathological statuses, the up-regulation of miR-150 in macrophages promotes the migration of blood vessel endothelial cells, so that the progression of atherosclerosis is accelerated, and conditions including obesity, hyperglycemia and chronic inflammation are further caused by blood vessel damage.

Therefore, it is indicated that if the content of miR-150 in the cellular MVs of macrophages is down-regulated, the promoting effect on the endothelial cell migration capability shall be inhibited, and the occurrence and progression of the above-mentioned conditions shall be postponed, thus atherosclerosis can be cured.

In the present example, the content of miR-150 in the THP-1 cellular MVs is down-regulated, and the effect on the endothelial cell migration capability from the THP-1 cell MVs is accessed by introducing the anti-sense RNA of miR-150.

The specific steps include:
(1) down-regulating miR-150 content in the THP-1 cellular MVs by introducing anti-sense RNA reference to the method as applied in example 6;
(2) separating and preparing THP-1 cellular MVs with the method as applied in example 2;
(3) incubating the HMEC-1 cells with THP-1 cellular MVs for 6 h; and
(4) detecting the c-myb protein quantity and the migration capability of HMEC-1 cells with the method as applied in example 7.

Figure 8E:
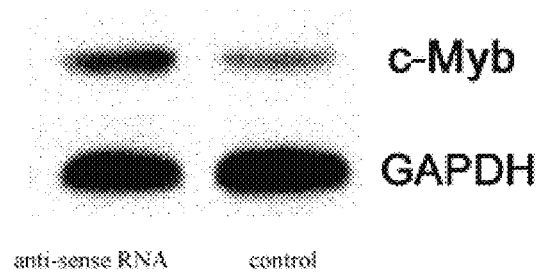
FIG. 8E shows that the protein expressions of target cells, HEMC-1 cells, can be influenced by regulating the quantity of miRNAs in THP-1 cellular MVs.
Figure 8F:
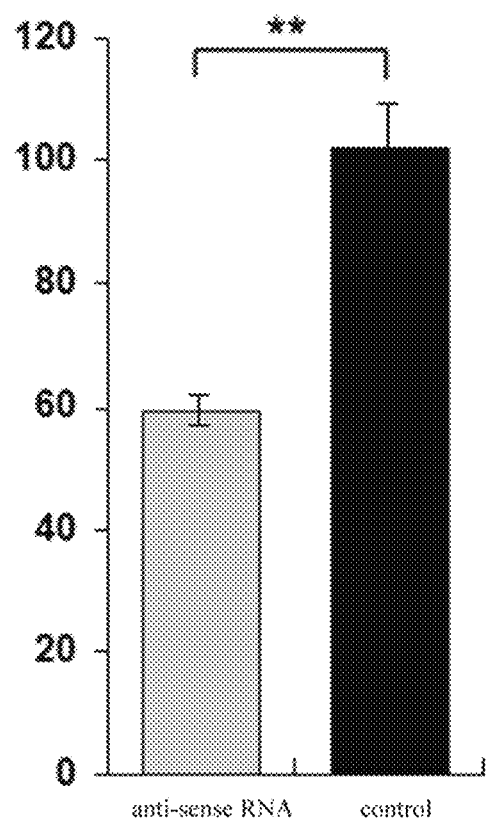
FIG. 8F shows that the migration ability of target cells, the HMEC-1 cells, can be influenced by regulating the quantity of miRNAs in THP-1 cellular MVs.

The c-myb content in HMEC-1 cells is shown in FIG. 8E, which shows that, compared with normal THP-1 MVs (control), the THP-1 MVs with down-regulated miR-150 (the anti-sense RNA) can obviously promote the c-myb expression in HMEC-1 cells. The migration capability of HMEC-1 cells is shown in FIG. 8F, which shows that compared with normal THP-1 MVs (control), the THP-1 MVs with down-regulated miR-150 (the anti-sense RNA) can obviously inhibit the migration capability of HMEC-1 cells.

Due to that during the treatment of atherosclerosis, the up-regulation of miR-150 in macrophage MVs promotes the migration of blood vessel endothelial cells and causes blood vessel damage, thus accelerates the progression of atherosclerosis and causes the occurrence of conditions including obesity, hyperglycemia and chronic inflammation; it is indicated that, theoretically if the content of miR-150 in the cellular MVs of macrophages is down-regulated, the occurrence and progression of atherosclerosis shall be postponed, and the disease can be prevented and cured. The inventors have adopted the macrophage cell line (THP-1) and the endothelial cell line (HMEC-1) to simulate the in vivo interaction between macrophages and endothelial cells. The simulation results prove that the migration capability of HMEC-1, target cells of miR-150 from THP-1 cells, can be inhibited by down-regulating the miR-150 content in THP-1 cells.

Therefore, the prevention and treatment of disease can be achieved by modulating (up or down-regulating) the content of certain miRNAs in cellular MVs.

The invention claimed is:
1. A method for treating atherosclerosis, comprising modulating the content of miR-150 of human beings or animals in vivo with the anti-sense of miR-150, characterized in that, the method for modulating the content of miR-150 comprises:
 (1) modulating the content of the anti-sense of miR-150 in donor cell microvesicles (MVs);
 (2) separating the donor cellular MVs; and
 (3) introducing the separated cellular MVs into the human beings or animals.

2. The method according to claim 1, characterized in that, the modulation of the content of miR-150 is related to the occurrence and/or progression of atherosclerosis.

3. The method according to claim 1, characterized in that, the technique to separate cellular MVs can be one or more selected from the group consisting of differential centrifugation, immune adsorption and ultra-filtration.

4. The method according to claim 3, characterized in that, the differential centrifugation includes the following steps:
 (1) conducting centrifugation on the cell culture, tissue or body fluid at the rotating speed of 300g for 5 min, and collecting the first supernatant;
 (2) conducting centrifugation on the first supernatant at the rotating speed of 1,500g for 20 min, and collecting the second supernatant;
 (3) conducting centrifugation on the second supernatant at the rotating speed of 10,000 g for 30 min, and collecting the third supernatant; and
 (4) conducting centrifugation on the third supernatant at the rotating speed of 110,000g for 70 min, and the donor cellular MVs are in the sediment.

5. The method according to claim 3, characterized in that, the immune adsorption includes the following steps:
 (1) conducting centrifugation on cell culture medium, tissue or body fluid at the rotating speed of 3,000g for 30 min, and collecting supernatant; and
 (2) incubating the supernatant in the tissue culture plate adsorbed with cell-specific antibodies or immunomagnetic beads for 30-60 min, and collecting the adsorbed cellular MVs.

6. The method according to claim 3, characterized in that, the ultra-filtration includes the following steps:
 (1) conducting centrifugation on the cell culture, tissue or body fluid at the rotating speed of 3,000g for 30 min, and collecting supernatant; and
 (2) adding the supernatant into the concentration centrifugation tube with 100 KD filter films, and the cellular MVs can be obtained through conduct centrifugation and concentration at the rotating speed of 4,000 rpm.

* * * * *